United States Patent [19]
Uckun

[11] Patent Number: 5,911,995
[45] Date of Patent: *Jun. 15, 1999

[54] EGF-GENISTEIN CONJUGATES FOR THE TREATMENT OF CANCER

[75] Inventor: Fatih M. Uckun, White Bear Lake, Minn.

[73] Assignee: Regents of the University of Minnesota, Minneapolis, Minn.

[*] Notice: This patent is subject to a terminal disclaimer.

[21] Appl. No.: 08/602,186

[22] Filed: Feb. 16, 1996

Related U.S. Application Data

[63] Continuation-in-part of application No. 08/293,731, Aug. 19, 1994, Pat. No. 5,587,459.

[51] Int. Cl.⁶ .................. A61K 39/385; A61K 39/00; C07K 16/00; A01N 61/00
[52] U.S. Cl. .................. 424/195.11; 424/185.1; 424/192.1; 424/193.1; 530/391.7; 514/2; 514/4
[58] Field of Search ............... 530/391.1, 391.7, 530/391.9, 388.75, 325, 345; 424/181.1, 195.11, 185.1, 192.1, 193.1; 514/4, 12, 2

[56] References Cited

U.S. PATENT DOCUMENTS 5,587,459  12/1996  Uckun .................. 530/391.1

FOREIGN PATENT DOCUMENTS

| 61-246124 | 11/1986 | Japan . |
| 3-275625 | 12/1991 | Japan . |
| WO 88 00837 | 2/1988 | WIPO . |
| WO 93 20834 | 10/1993 | WIPO . |
| WO 94/18345 | 8/1994 | WIPO . |
| WO 95 01806 | 1/1995 | WIPO . |
| WO 95/02187 | 1/1995 | WIPO . |
| WO 95/07348 | 3/1995 | WIPO . |
| WO 93/23069 | 11/1995 | WIPO . |
| WO 94/26891 | 11/1995 | WIPO . |
| WO 96 06116 | 2/1996 | WIPO . |

OTHER PUBLICATIONS

Emmis BW. Cancer Investigation 9(5): 553–562,1991.
Lyall RM et al Cancer Research 47: 2961–2966, 1987.
Abrams, et al. *Cancer* 74(3 Supp):1164–76 (1994).
Adlercreutz, et al. *Am. J. Clin. Nutr.* 54: 1093–1100 (1991).
Adlercreutz, et al. *Lancet*, 342, 1209 (1993).
Arteaga, et al. *Cancer Res.* 54:4703–09 (1994).
Aullo et al. *The EMBO Journal*, 11(2), 575–583 (1992).
Avila et al. *Cancer Res.*, 54:2424–2428 (1994).
Baselga et al. *Breast Cancer Res. and Treatment*, 29:127–138 (1994).
Baselga et al. *J. Nat'l Cancer Inst.*, 85:1327–33 (1993).
Batra et al. *Proc. Nat. Acad. Sci. USA*, 89, 5867–5871 (Jul. 1992).
Batra et al. *The Journal of Biological Chemistry*, 265(25), 15198–15202 (Sep. 5, 1990).
Bennett et al. *PNAS USA*, 91, 3127 (1994).
Berchuch et al. *Am. J. Obest. Gynec.*, 164:669–674 (1991).
Bolen et al. *Adv. Can Res.*, 57, 103 (1991).
Bolen *Cell Growth & Diff.*, 2:409–414 (Aug. 1991).
Bolen et al. *FASEBJ*, 6:3403–7 (Dec. 1992).
Bolognesi et al. *Clin. Exp. Immunol.* 89, 341 (1992).
Bonadonna et al. *JAMA*, 273:542–7 (Feb. 1995).
Campbell et al. *EMBO J.*, 9, 2125 (1990).
Canevari et al. *Annals. of Oncology*, 5, 698–701 (1994).
Carpenter et al. *J. Biol. Chem.*, 265:7709–12 (1990).
Chal et al. *Cancer Res.*, 53:447–451 (Feb. 1993).
Ching et al. *Mol. Cell Biochem.*, 126:151–158 (1993).

(List continued on next page.)

*Primary Examiner*—Sheela Huff
*Assistant Examiner*—Yvonne Eyler
*Attorney, Agent, or Firm*—Merchant, Gould, Smith, Edell, Welter & Schmidt, P.A.

[57] ABSTRACT

A conjugate formed of epidermal growth factor covalently linked to a tyrosine kinase inhibitor, such as genistein, and a method for killing cancer cells, in vivo and in vitro, by administering a cytotoxic dose of an epidermal growth factor tyrosine kinase inhibitor conjugate.

12 Claims, 15 Drawing Sheets

OTHER PUBLICATIONS

Chrysogelos et al. *Breast Cancer Res. & Tmt.*, 29:29–40 (1994).
Clavel et al. *Eur. J. Cancer*, 29A–598–604 (1993).
Cohen et al. *J. Urology*, 152:2120–2124 (Dec. 1994).
Connolly et al. *The Prostate*, 20:151–158 (1992).
Constantinou et al. *Cancer Res.*, 50, 2618 (1990).
Cushman et al. *J. Med. Chem.*, 37:3353–3362 (1994).
Cushman et al. *J. Med. Chem.*, 34:798–806 (1991).
Dean et al. *Int. J. Cancer*, 8:103–107 (1994).
deWit et al. *JI Investig. Dermatology*, 99:168–173 Aug. 1992).
Dunphy et al. *Cancer*, 73:2157–67 (Apr. 1994).
Embleton et al. *Br. J. Cancer*, 63, 670–674 (1991).
Fong et al. *Cancer Res.* 52:5887–5892 (Nov. 1992).
Fox et al. *Breast Cancer Res. & Tmt.*, 29:41–9 (1994).
Fu et al. *Cardiovascular Research*, 27, 1691–1697 (1993).
Fukuzawa et al. *Biochem. Pharmacol.*, 42, 1661–1671 (1991).
Gasparini et al. *Breast Cancer Res. & Tmt.*, 29:59–71 (1994).
Gorgoulis et al. *AntiCancer Res.*, 12:1183–88 (1992).
Gottstein et al. *Annals of Oncology*, 5, S97 (1994).
Grossbard et al. *Important Advances in Oncology*, pp. 112–136 (1992).
Grossbard et al., "Immunotoxin Therapy of Malignancy", pp. 111–131, 1989.
Gullick *Br. Med. Bull.*, 47:87–98 (1991).
Gunther et al. *Leukemia*, 7:298–309 (Feb. 1993).
Harris *Cancer Cells*, 2(10), 321–323 (Oct. 1990).
Heimbrook et al. *Journal of Industrial Microbiology*, 7, 203–208 (1991).
Hertler et al. *J. Clin. Oncol.*, 7, 1932 (1989).
Hirono et al. *Oncology*, 52:182–188 (1995).
Hölting et al. *E.J. Endocrinology*, 132–229–35 (1995).
Honma et al. *Cancer Res.*, 52:4017–4020 (Jul. 1992).
Houston et al. *Immunoconjugates, Antibody–Conjugates in Radioimaging and Therapy of Cancer*, pp. 71–96 (1987).
Hunter et al. *Annu. Rev. Biochem.*, 54, 897 (1985).
Huston et al. *Intern. Rev. Immunol.*, 10, 195–217 (1993).
Hwu et al. *The Journal of Experimental Medicine*, 178, 361–366 (Jul. 1993).
Irvin et al. Meeting Abstract, *International Association for Comparative Research on Leukemia and Related Diseases*, 16th Symposium Jul. 11–16, 1993, Montreal, Quebec, Canada.
Kersey et al. Abstract of presentation at symposium to Honor. G. and E. Klein, Omaha, NE, May 1991.
Khazaie et al. *Cancer & Metastasis Revs.*, 12:255–74 (1993).
Kirk et al. *Br. J. Cancer*, 69:988–994 (1994).
Klijn et al. *Cancer Res. & Treat.*, 29:73–83 (1994).
Lee et al. *Protein Engineering*, 6(4), 433–440 (1993).
Lipponen *Br. J. Cancer*, 69:1120–1124 (1994).
Lorberboum–Galski et al. *The Journal of Biological Chemistry* 263(35), 18650–56 (Dec. 15, 1988).
Markovits et al. 21st Ann. Mtg. Am. Assoc. Cancer Res., May 23–26, 1990, Wash, D.C.
Maygarden et al. *Modern Pathology*, 7:930–936 1994).
Mendelsohn et al. In: *Biologic Therapy of Cancer: Principles and Practice*, pp. 607–623 (1995).
Mendelsohn *J. Nat'l Cancer Inst.*, 13:125–131 (1992).
Mesri et al. *The Journal of Biological Chemistry*, 268(7), 4853–4862 (Mar. 5, 1993).
Modjtahedi et al. *Br. J. Cancer*, 67:254–261 (1993).
Mueller et al. *Cancer Res.*, 51:2193–98 (1991).
Mukaida et al. *Cancer*, 68:142–148 (1991).
Muthuswany et al. *Mol. Cell Biol.*, 14:735–743 (Jan. 1994).
Naramura *Cancer Immunol. Immunother.*, 37:343–349 (1993).
Okabe et al. *Blood*, 80:1330–1338 (Sep. 1992).
Okabe et al. *Leukemia & Lymphoma*, 12:41–49 (1993).
Otani et al. *J. Biol. Chem.*, 268, 22733 (Oct. 21, 1993).
Ottenhoff–Kalff et al. *Cancer Res.*, 52:4773–8 (Sep. 1992).
Pai et al. *Cancer Research*, 51, 2808–2812 (Jun. 1, 1991).
Pastan et al. *Cell*, 47, 641 (1986).
Pastan et al. *Science*, 254, 1173–1177 (Nov. 22, 1991).
Pastan et al. *The Journal of Biological Chemistry*, 264(26), 15157–15160 (Sep. 15, 1989).
Pelham et al. *Eur. J. Biochem.*, 67, 247 (1976).
Perentesis et al. Abstract AI–00793 (Sep. 1, 1987).
Perentesis et al. Abstract CA–53586 (Mar. 1, 1993).
Perentesis et al. *Biofactors*, 3 (1991/92).
Perentesis et al. *PNAS USA*, 85, 8386 (1988).
Pickering et al. *J. Clin. Invest.*, 91, 724–729 (Feb. 1993).
Piontek et al. *AntiCancer Res.*, 13:2119–2124 (1993).
Scheuermann et al. *PNAS USA*, 91, 4048–4052 (1994).
Schnürch et al. *E. J. Cancer*, 30A:491–496 (1994).
Scholar et al. *Cancer Letters*, 87:159–162 (1992).
Shaw et al. *The Journal of Biological Chemistry*, 266(31), 21118–21124 (Nov. 5, 1991).
Spinozzi et al. *Leuk. Res.*, 18, 431 (1994).
Takekara et al. *Int. J. Cancer*, 47:938–942 (1991).
Theuer et al. *Journal Biolog. Chemistry*, 267(24), 16872–16877 (Aug. 25, 1992).
Thomas *Drugs of Today*, 28:311–331 (1992).
Toi et al. *Eur. J. Cancer*, 26:722–724 (1990).
Traganos et al. *Cancer Res.*, 52, 6200 (1992).
Trail, et al. *Science* 261:212 (Jul. 1993).
Uckun *Antibody Immunoconjugates and Radiopharmaceutics*, 1, 247 (1988).
Uckun et al. *Blood*, 71 13 (1988).
Uckun *Brit. J. Haematol.*, 85, 435 (Nov. 9, 1993).
Uckun Grant No. 1U01CA61549–01—B43(Anti–CD19)–Pokeweed Antiviral Protein Immunotoxin (1994).
Uckun et al. *Int. J. Radiat. Biol.*, 56, 611–615 (1989).
Uckun et al. *J. Immunol.*, 134, 2010 (1985).
Uckun et al. *Leukemia*, 7, 341 (Feb. 1993).
Uckun et al. *PNAS USA*, 90, 252 (Jan. 1993).
Ullrich et al. *Cell*, 61:203–212 (Apr. 1990).
Vitetta et al. *Biologic Therapy of Cancer*, pp. 482–495 (1991).
Vitetta et al. *Cancer Res.*, 51, 4052–4058 (Aug. 1, 1991).
Vietta, et al. *Science* 225:1098–1104 (1984).
Wada et al. *Cancer Research*, 48, 2273 (1988).
Wingo et al. *A Cancer J. for Clinicians*, 45, 8–30 (Jan./Feb. 1995).
Yamanashi et al. *Science*, 251:192–194 (Jan. 1991).

FIG. 1
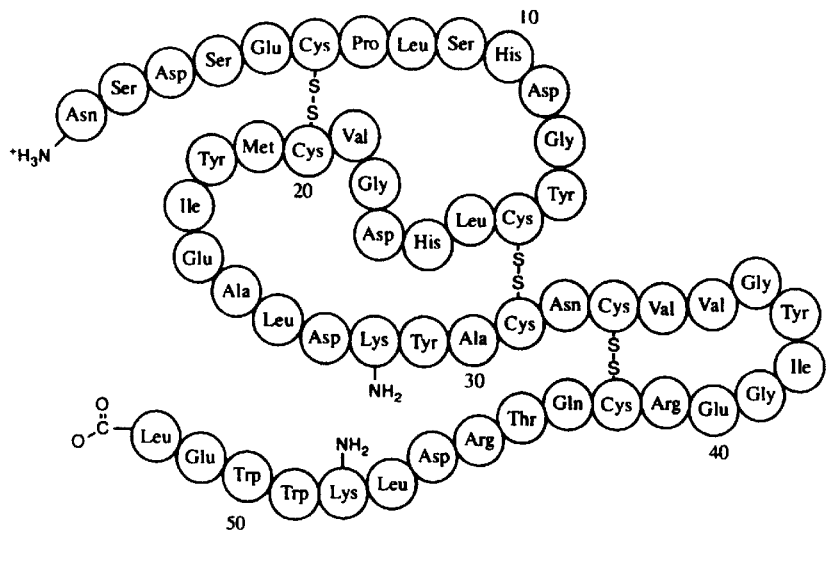
rh EGF
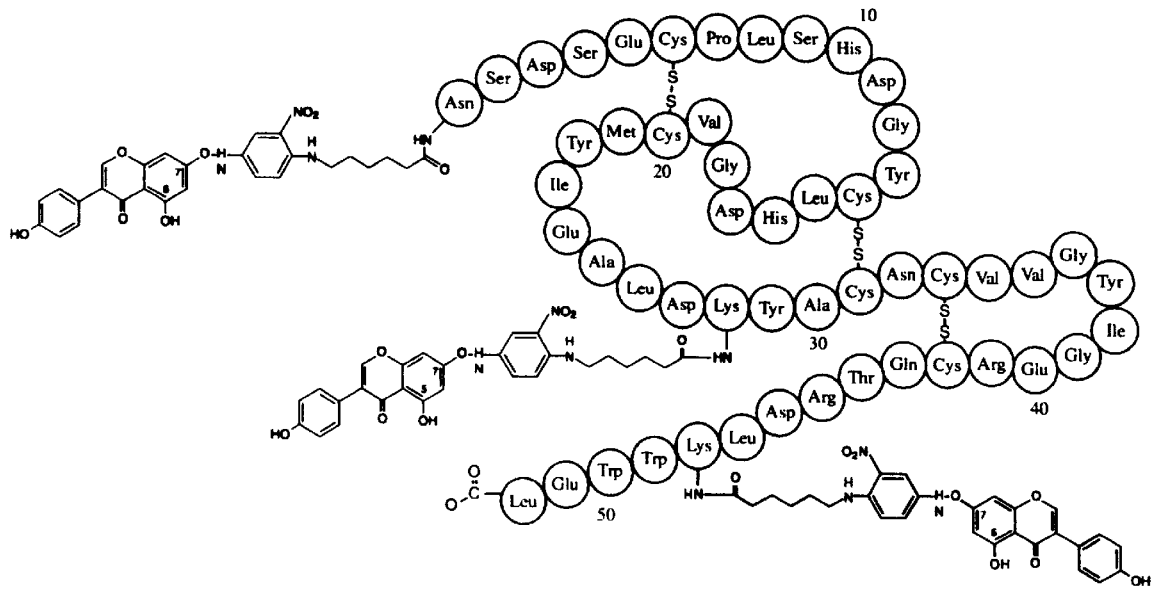

FIG. 2
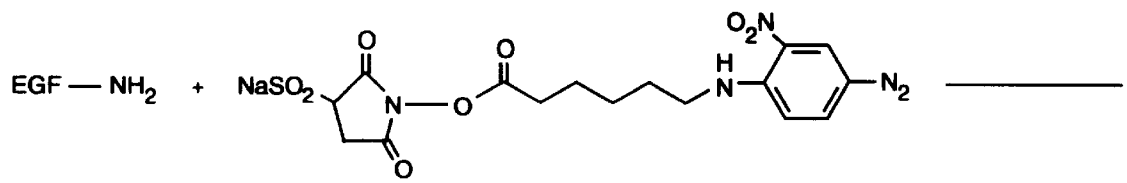
Sulpho-SANPAH
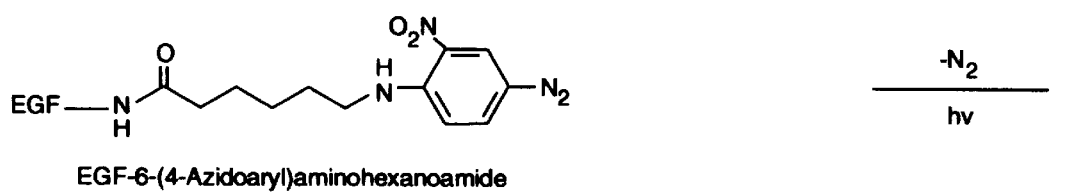
EGF-6-(4-Azidoaryl)aminohexanoamide
$\xrightarrow{-N_2}{h\nu}$
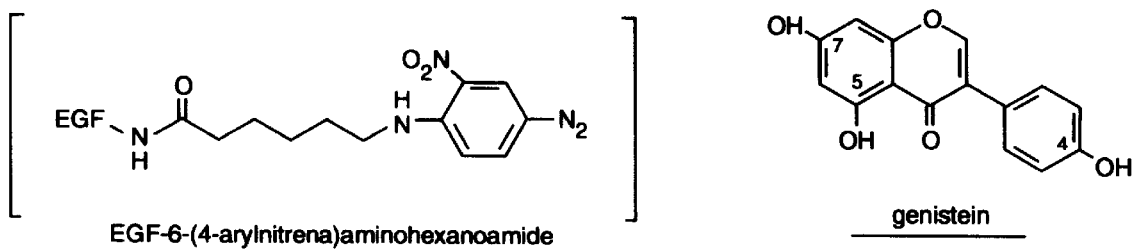
EGF-6-(4-arylnitrena)aminohexanoamide     genistein
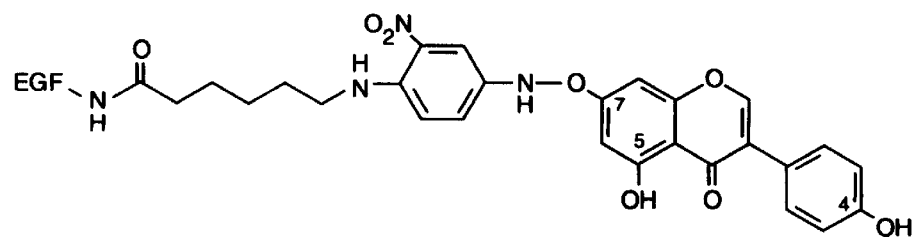

APT Blot

APT Blot

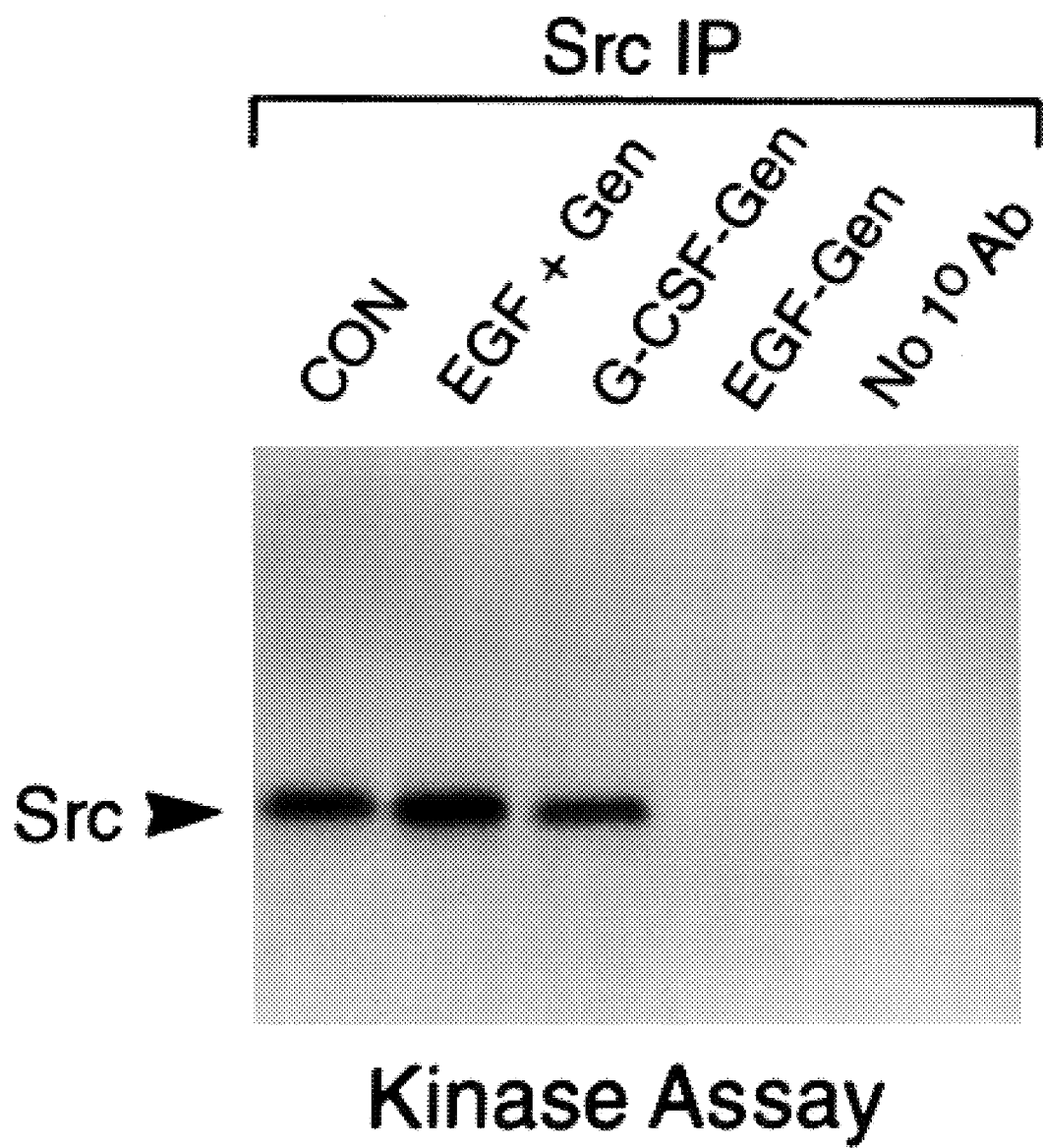

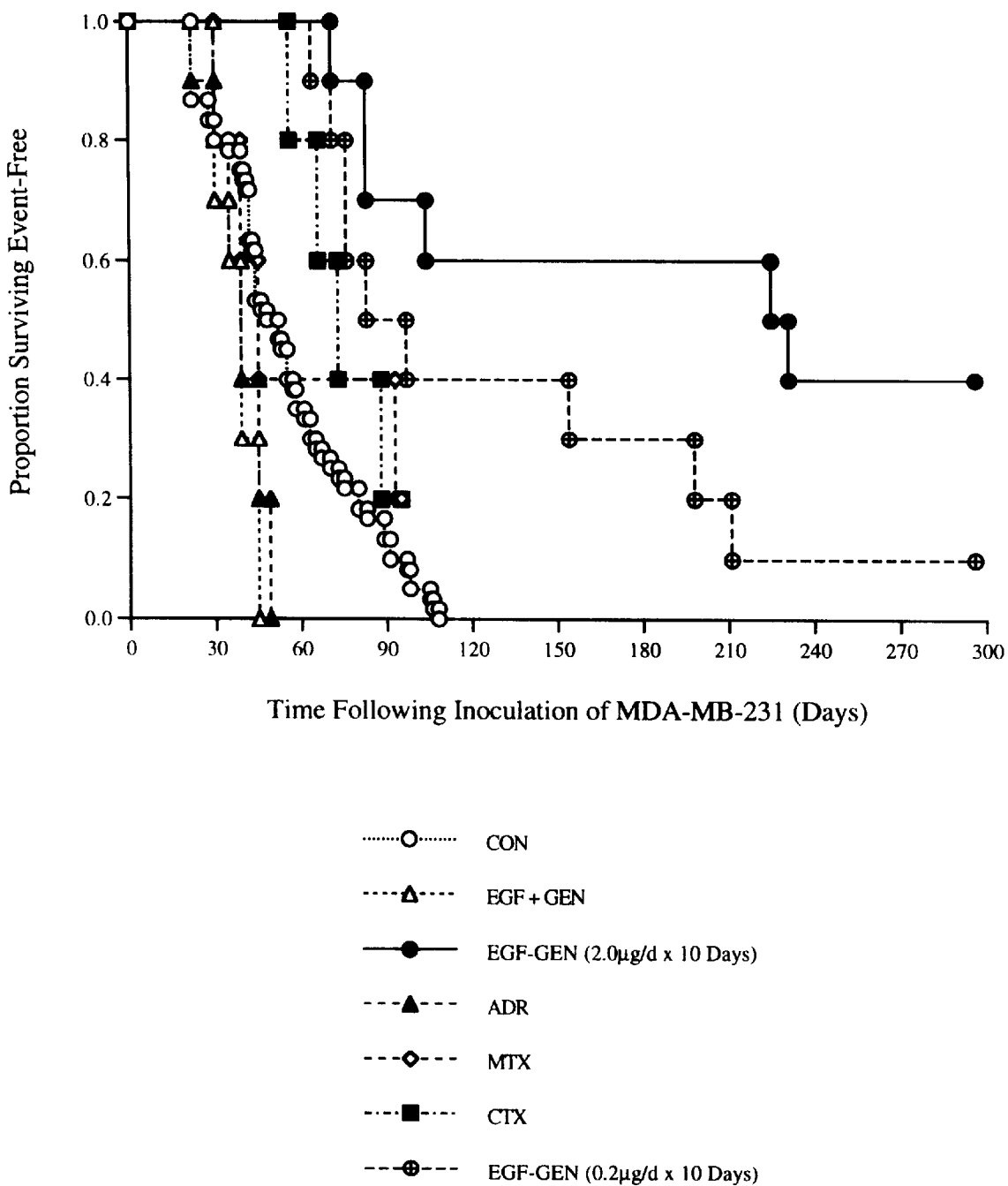

EGF-GENISTEIN CONJUGATES FOR THE TREATMENT OF CANCER

This invention is a continuation-in-part of U.S. patent application Ser. No. 08/293,731 filed Aug. 19, 1994 now issued as U.S. Pat. No. 5,587,459.

FIELD OF THE INVENTION

This invention relates to compositions and methods for the treatment of cancer, more particularly to compositions comprising EGF linked to a tyrosine kinase inhibitor.

BACKGROUND OF THE INVENTION

Cancer is the leading cause of death, second only to heart disease in both men and women. In the fight against cancer, numerous techniques have been developed and are the subject of current research to understanding the nature and cause of the disease, and to provide techniques for control or cure thereof.

Breast cancer is the most common tumor in women, representing 32% of all new cancer cases and causing 18% of cancer-related deaths of women in the United States. It is estimated that in 1995 a total of 183,400 new patients were diagnosed with breast cancer and 46,240 of these will die of this disease. In women, breast cancer is the second major cause of cancer deaths. Although the five-year survival rate for localized breast cancer has risen from 78% in the 1940's to 93% today, if the cancer has spread with distant metastases at the time of diagnosis, the five-year survival rate is only 18%. Thus, currently, a major challenge in the treatment of breast cancer is to provide a cure for patients who have advanced metastatic disease. Although metastatic breast cancer is sensitive to chemotherapy, it remains incurable with contemporary therapeutic approaches. While a majority of patients experience an initial response, their overall survival is only modestly improved. The development of new and potent anti-breast cancer drugs and the design of treatment protocols utilizing these new agents is an exceptional focal point for research in the modern therapy of breast cancer.

Drug targeting is a potentially attractive new approach to killing malignant cells, while leaving normal tissue unharmed. The advent of hybridoma technology made the supply of monoclonal antibodies limitless. Monoclonal antibodies linked to bioactive agents form immunoconjugates, combining selectivity of the carrier moiety with potency of the bioactive moiety.

For the past decade, immunoconjugates have been under investigation for the treatment of various cancers. Although these agents have shown some potential to provide safe and effective therapy for human disease, many difficulties remain. Ideally, consistently locateable and reliable markers on target cells would permit the binding portion of an immunoconjugate to completely avoid non-target tissues. In reality, however, cross reactivity with antigens expressed by vital life-maintaining organs can give rise to unacceptable complications. Patients may also develop immune responses to the separate components of the immunoconjugate. Moreover, cytotoxicity solid tumor penetration, and relapse caused by residual disease present treatment problems. Therefore, there is a continuing need for improved agents and methods of their use in targeting and inhibiting or eliminating cell populations associated with metastatic disease.

The human epidermal growth factor (EGF) is a six kilodalton (kDa), 53 amino acid, single-chain polypeptide which exerts its biological effect by binding to a specific 170 kDa cell membrane receptor (EGF-Rc). The human EGF-Rc consists of an extracellular domain with a high cysteine content and N-linked glycosylation, a single transmembrane domain, and a cytoplasmic domain with tyrosine kinase activity.

Many types of cancer display enhanced EGF-Rc expression on their cell surface membranes. Enhanced expression of the EGF-Rc can increase signalling via receptor-mediator pathways which lead to pleiotropic biological effects including excessive proliferation and metastases. Examples include prostate cancer, breast cancer, lung cancer, head and neck cancer, bladder cancer, melanoma, and brain tumors. In breast cancer, expression of the EGF-Rc is a significant and independent indicator for recurrence and poor relapse-free survival. The epidermal growth factor receptor (EGF-Rc) on cancer cells therefore represents a potential target for biotherapy.

Activation of the proliferative pathways by protein tyrosine kinases has been suggested to play a role in the development and progression of various types of human cancer. For example, SRC kinase has been suggested to play a role in the pathogenesis of breast cancer, the enzymatic activity of SRC in breast cancer being significantly higher when compared to benign or normal breast tissues.

Genistein, an isoflavone (5, 7, 4'-trihydroxyisoflavone) from fermentation broth of Pseudomonas, is a naturally occurring tyrosine kinase inhibitor present in soy beans. Genistein, at very high concentrations, which is not achievable in vivo, has been shown to inhibit the in vitro proliferation of cancer cells, including human breast cancer cells (Monti et al., 1994, *AntiCancer Res.*, 14:1221–1226) and prostate cancer cells (Peterson et al., 1993, *Prostate* 22:335–345).

Genistein is generally known as a weak tyrosine kinase inhibitor which only reversibly inhibits tyrosine kinase (Levitzki and Gazit, *Science* 267:1782–1788, 1995). Furthermore, genistein has been demonstrated to prevent "death" signals triggered by enhanced tyrosine kinase activity, including radiation-induced cell death, (Uckun et al., PNAS, USA 89:9005, 1992).

Genistein and similar isoflavones do not easily enter cells, and its delivery to cancer cells in non-toxic doses presents problems for therapeutic use. While genistein and similar tyrosine kinase inhibitors function well against cancer cells in vitro, such effects are observed at very high concentrations not achievable in vivo without excessive toxicity. Therefore, despite potent inhibition of TK activity in vitro, many TK inhibitors, including genistein, have shown little or no TK inhibitory activity, in vivo (Levitzki and Gazit, 1995, Science 267:1782–1788). Genistein, a pure competitive inhibitor of ATP, has been demonstrated as inhibitory only in the 10–100 $\mu$M range in tissue culture, and showed no efficacy in vivo.

Although the prior art suggests various types of therapeutic models for the treatment of metastatic disease, including breast cancer, to date useful agents have not been adequately demonstrated. There remains a need for specific and effective therapeutic agents for the treatment of metastatic disease.

SUMMARY OF THE INVENTION

The present invention provides a conjugate comprising a tyrosine kinase (TK) inhibitor, preferably an isoflavone tyrosine kinase inhibitor, covalently linked to epidermal growth factor (EGF). The conjugate of the invention specifically binds to EGF receptors (EGF-Rc) associated with vital tyrosine kinases in cancer cells. Upon binding of inventive conjugate to EGF-Rc on cancer cells, the isoflavone tyrosine kinase inhibitor acts to inhibit the EGF-Rc kinase and associated Src family tyrosine kinases, and to kill the target cancer cells without affecting normal cells, including those normal cells that bear EGF-Rc.

The specific association of EGF with an isoflavone tyrosine kinase inhibitor such as genistein surprisingly elicited more than 99% killing of cancer cells expressing the EGF-Rc, and also remarkably improved tumor-free survival time in vivo as compared with combination therapy comprising these same agents in unconjugated form.

Conjugates of EGF-genistein were found to bind with high affinity to the EGF receptor on breast cancer cells and trigger their rapid apoptotic cell death, killing greater than 99.99% of colonogenic breast cancer cells in vitro. Furthermore, EGF-genistein was shown to be very well tolerated by SCID mice, as well as monkeys, and showed potent anti-tumor activity against breast cancer xenografts.

The instant invention comprises an isoflavone tyrosine kinase inhibitor such as genistein covalently linked to epidermal growth factor. The EGF-tyrosine kinase inhibitor conjugates of the present invention unexpectedly induced remarkable levels of apoptotic death in target cancer cells both in a specific and efficient manner.

In one embodiment, the invention provides a unique conjugate having multiple genistein molecules, for example 6 genistein molecules attached to a single EGF molecule.

BRIEF DESCRIPTION OF THE DRAWINGS

FIG. 1 is a schematic representation of the primary structure of recombinant human EGF and its linkage to genistein. There are three available lysine (Lys) residues in EGF which represent the attachment sites for genistein.

FIG. 2 is a schematic representation of a two-step photochemical method for the synthesis of genistein.

FIG. 4A is an antiphosphotyrosine (APT) Western blot analysis of whole cell lysates; and FIG. 4B is an APT Western blot analysis of EGF-Rc immune complexes.

FIG. 5 is an autoradiogram of an in vitro Src immune complex kinase assay showing autophosphorylation of BT-20 cellular Src kinase after overnight treatment with EGF-genistein or control compounds.

FIG. 9 is a graph showing the effects of EGF-genistein and control compounds on the survival of SCID mice xenografted with human breast cancer cells.

DETAILED DESCRIPTION OF THE INVENTION

Figure 3:
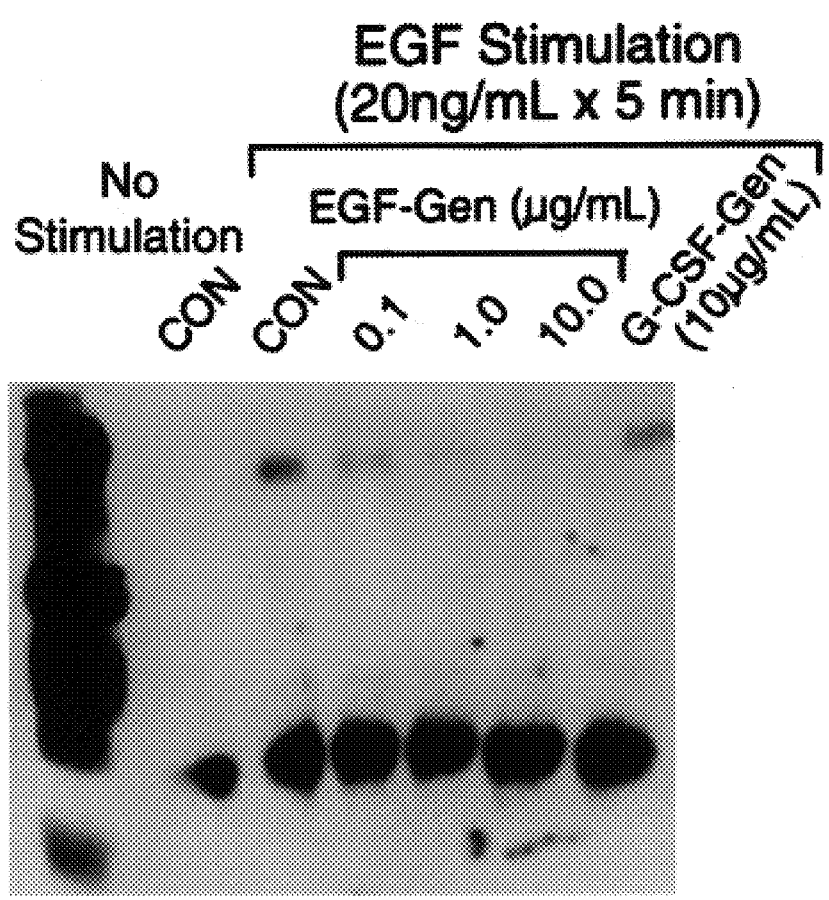
FIG. 3 is an autoradiogram of a Western blot showing autophosphorylation of MDA-MB-231 cellular EGF-Rc in response to EGF stimulation after overnight treatment with EGF-genistein or control compounds.

EGF-receptor (Rc) in human cancer cells associates with vital tyrosine kinases, including members of the Src protooncogene tyrosine kinase family such as Src and Fyn. These membrane-associated complexes are vital regulators of cancer cell survival and prevention of programmed cell death ("apoptosis"). Compositions designed to inactivate these membrane-associated anti-apoptotic EGF-Rc/tyrosine kinases, such as the inventive compositions demonstrated in the present application, have great potential as a new generation of potent and non-toxic anti-cancer compositions.

A preferred embodiment of the present invention is directed to an EGF-isoflavone conjugate, preferably EGF-Genistein, that binds to EGF-Rc present on the surface of cancer cells and induces apoptotic cell death. Without limiting the scope of the invention, apoptotic cell death results from inactivating the above-mentioned cell survival machinery.

Protein tyrosine kinases have been long suspected to play pivotal roles in regulation of cell survival in human cancer cells. While tyrosine phosphorylation has been reported as having a role in cell proliferation and cell transformation, little or no information relating to specific tyrosine kinases and their relationship to cell survival is known. More recently, a series of studies provided direct evidence that tyrosine kinases indeed do play important roles regulating cell death. Following the initial discovery that ionizing radiation-induced programmed cell death (=apoptosis) is triggered by tyrosine kinase activation and that genistein, an inhibitor of protein tyrosine kinases, prevented radiation-induced cell death (Uckun, et al., *PNAS USA* 89:9005, 1992), other cellular death signals were shown to be triggered by tyrosine kinases and prevented by tyrosine kinase inhibitors, such as genistein or herbimycin A. Cohen, et al. reported that HIV-1 induced death of T-cells is prevented by tyrosine kinases inhibitors, providing evidence that tyrosine kinases trigger AIDS-virus induced cytotoxicity to human T cells (Cohen, et al., *Science* 256: 542, 1992). Lee, et al. reported that apoptosis and cell death in thymocytes treated with dexamethasone were inhibited by the tyrosine kinase inhibitor herbimycin A (Lee, et al., *BBRC* 202:128, 1994). Migita, et al. reported that anti-CD3 monoclonal antibody induced apoptosis of thymocytes is prevented by tyrosine kinase inhibitors (Migita, et al., *J. Immunol.* 153: 3457, 1994). Similarly, Ji, et al. reported that tumor necrosis factor alpha and ceramide-induced apoptosis is prevented by the tyrosine kinase inhibitor herbimycin A (Ji, et al., *BBRC* 212: 640, 1995). Notably, Eischen, et al. reported that several tyrosine kinase inhibitors, but most effectively genistein and herbimycin A, prevent Fas-induced apoptosis (Eischen, et al., *J. Immunol.* 153:1947, 1994; see FIG. 4 on page 1951 for inhibition of apoptosis by genistein), a finding which was further confirmed by Anel, et al. (Anelet, et al., *Eur. J. Immunol.* 24:2469, 1994). Similarly, Liu, et al. reported that genistein reduces taxol-induced apoptosis of human ovarian cancer cells 10-fold (Liu, et al., *Biochem. Pharmacol.* 48:1265, 1994; see FIG. 2 on page 1268 and 4th paragraph on the same page for inhibition of apoptosis by the tyrosine kinase inhibitor genistein).

However, there are also membrane-associated receptor-tyrosine kinase complexes which have anti-apoptotic functions, such as the CD19 receptor on childhood leukemia cells (Myers, et al., *Proc. Nat'l. Acad. Sci. USA* 92:9575–9579, 1995). Thus, while some of the tyrosine kinases are important for initiation of death signals, others may have opposite functions and protect the cell from various death signals. Currently, very little is known about the identity of the specific tyrosine kinases responsible for initiation of death signals or those that protect the cell from death signals. If one could identify vital tyrosine kinases or vital anti-apoptotic protein complexes containing tyrosine kinases whose anti-death function depends on the enzymatic activity of the contained tyrosine kinase, inactivation of such kinases could lead to cell death. Since the same tyrosine kinase and many other tyrosine kinases may also exert opposite functions in different compartments of the cell, it is absolutely essential to deliver an inactivating agent, such as a tyrosine kinase inhibitor, only to those tyrosine kinases which play a pivotal role in an anti-death machinery, if one aims at destroying the cell.

For example, CD19 receptor associated tyrosine kinases within that membrane associated anti-apoptotic complex can be inactivated by delivering the tyrosine kinase inhibitor genistein to CD19 receptor using an anti-CD19 monoclonal antibody as a carrier molecule. As described in co-pending U.S. patent application Ser. No. 08/293,731, applicant has shown that genistein conjugate of B43 (anti-CD19) monoclonal antibody triggers apoptotic cell death in childhood leukemia cells.

While EGF-Rc is expressed on cancer cells, it is also expressed in numerous normal tissues. Thus, EGF-Rc is by no means a cancer-specific receptor. Therefore, the use of EGF-Rc as a target for immunotoxin or fusion toxin therapy to deliver a cytotoxic substance to cancer cells by using the EGF-Rc as a gate, would be expected to cause major side effects to multiple organs, in particular liver and gut toxicity because of high level expression of EGF-Rc in these tissues. For example, a ricin A chain immunotoxin of the anti-EGF-Rc antibody 528IgG1, was very toxic in vivo (Taetle, et al., *J. Nat'l. Cancer Inst.* 80:1053–1059, 1988; Ennis, et al., *Cancer Investigation* 9:553–562, 1991).

Furthermore, several studies have demonstrated that EGF-Rc which has intrinsic tyrosine kinase is not essential for cancer cell survival, even though it may be involved in regulation of cell cycle progression. Inhibitors designed specifically to inhibit the EGF-Rc tyrosine kinases did not kill cancer cells and were able, even at the highest concentrations tested, which are not achievable in vivo without unacceptable toxicity, to only transiently slow down the proliferation of cancer cells.

Several inhibitors specific for EGF-Rc tyrosine kinase have been developed:

PD 153035, which was reported by Fry, et al. (Fry, et al. *Science* 265:1093–1095, 1994) inhibited EGF-Rc tyrosine kinase by 50% at a concentration (i.e., IC50) of 29 pM. In the same assay, when tested side-by-side, Genistein yielded an IC50 value of 1,179,000 pM. However, PD 153035 did not kill EGF-Rc positive cells.

BE-23372M, which was reported by Tanaka, et al. inhibited EGF-Rc tyrosine kinase with an IC50 value of 30 nM, whereas in side-by-side comparison Genistein had an IC50 value of 5,100 nM. However, this agent had very poor membrane penetrability. Even at concentrations as high as 25,000,000 nM, only 50% inhibition of cell growth was observed (Tanaka, et al., *Jpn. J. Cancer Res.* 85:253–259, 1994).

RG-13022, which was reported by Reddy et al, also elicited only a transient cytostatic effect on breast cancer cells even at 10,000 nM concentrations and its inhibitory effects were completely abolished after its removal from the culture medium (Reddy, et al., *Cancer Res.* 52:3636–3641, 1992).

Others also reported that inhibition of EGF-Rc tyrosine kinase with specific inhibitors elicits only transient cytostatic not cytotoxic effects on cancer cells (Yaish, et al., *Science* 242:933–935, 1988; Lyall, et al., *J. Biol. Chem.* 264:14503–14509, 1989; Levitzki and Gazit, *Science* 267:1782–11788, 1995).

By comparison, EGF-Genistein is a cytotoxic drug whose effects on cancer cells are not reversible. EGF-Genistein induced irreversible apoptotic death in human breast cancer cells and killed >99% of clonogenic cancel cells at 1 µg/mL (13.5 nM concentration for Genistein in conjugated form) concentrations.

In cancer cells, EGF-Rc associates with Src protooncogene family tyrosine kinases. If these complexes had anti-apoptotic function, and if they occurred only in cancer cells, or if were only vital (i.e., non-redundant) to cancer cells, then inactivation of these EGF-Rc tyrosine kinase complexes could theoretically be selectively cytotoxic to cancer cells. However, nothing is known from the published literature about the role of such EGF-Rc-tyrosine kinase complexes for survival of cancer cells versus normal cells.

The present invention provides direct evidence that EGF-Rc tyrosine kinase complexes are of vital importance for the survival of breast cancer and prostate cancer cells. Inactivation of these complexes with an EGF-Genistein conjugate triggers apoptosis in cancer cells and causes irreversible clonogenic cell death. More importantly, EGF-Genistein markedly improved the long-term tumor-free survival of immunodeficient SCID mice xenografted with metastatic human breast cancer and it was superior to methotrexate, adriamycin, as well as cyclophosphamide.

Remarkably, EGF-Genistein therapy was not associated with liver toxicity in mice, even though a substantial proportion of the injected EGF-genistein homed to the liver. Similarly, cynomologous monkeys treated with EGF-Genistein showed no clinical signs or laboratory evidence of any significant toxicity. Thus, even though EGF-Rc-tyrosine kinase complexes are essential for the survival of cancer cells, they are not critical for the survival of EGF-Rc positive normal tissues. Therefore, even though EGF-Rc is expressed not only on cancer cells but on many normal tissues as well, EGF-Genistein is a cancer specific drug which kills cancer cells by inactivation of life-maintaining enzyme complexes which are unique to cancer cells.

Protein Tyrosine Kinase Inhibitors

Genistein, an isoflavone (5,7,4'-trihydroxyisoflavone) derived from the fermentation broth of Pseudomonas species, is a naturally occurring, specific tyrosine kinase inhibitor present in soy beans, soy meal and tofu (Akiyama et al., *J. Biol. Chem.* 272:5592, 1987). Genistein is a fairly specific inhibitor for tyrosine kinases, having negligible inhibition activity against serine and threonine kinases (ogawara et al., *J. Antidiot.* (Tokyo), 39:606, 1986).

Daidzein (7,4'-dihydroxyisoflavone), other isoflavones isolated from soy, and biochanin A (4-methoxygenistein) are examples of additional isoflavone tyrosine kinase inhibitors that have been shown to inhibit proliferative growth of human breast cancer cell lines. (Peterson, et al., *BBRC* 179:661–667, 1991)

Genistein has been shown to prevent apoptosis in cells which have undergone ionizing radiation or engagement of the CD19 receptor (Uckun et al., *P.N.A.S. USA*, 89:9005, 1992). Since activation of protein tyrosine kinases is a mandatory step in both instances, this inhibition likely occurs primarily through genistein's PTK inhibitory properties on all PTK's in the cell, including those important to induction of cell death. The EGF-genistein conjugate of the present invention provides an unexpected result, the induction of apoptosis in a targeted cell by inhibiting only those tyrosine kinases which are associated with the EGF receptor and important for cell survival.

Genistein may be obtained commercially from Calbiochem (LaJolla, Calif.). Alternatively, genistein may be isolated from soybeans, soy meal, or tofu by the method described in Akiyama et al., *J. Biol. Chem.* 272:5592, 1987. Genistein is preferably synthesized by the method shown in FIG. 11, and as described in the example below.

Apoptosis

Apoptosis, or programmed cellular death, is an active process requiring new protein synthesis. Typically, the process requires ATP, involves new RNA and protein synthesis, and culminates in the activation of endogenous endonucleases that degrade the DNA of the cell, thereby destroying the genetic template required for cellular homostasis. Apoptosis is observed in controlled deletion of cells during metamorphosis, differentiation, and general cell turnover and appears normally to be regulated by receptorcoupled events. For these reasons, apoptosis has been called "programmed cell death" or "cell suicide". While every cell likely has the genetic program to commit suicide, it is usually suppressed. Under normal circumstances, only those cells no longer required by the organism activates this self-destruction program.

Apoptotic cell death is characterized by plasma membrane blebbing, cell volume loss, nuclear condensation, and endonucleolytic degradation of DNA at nucleosome intervals. Loss of plasma membrane integrity is a relatively late event in apoptosis, unlike the form of cell death termed necrosis, which can be caused by hypoxia and exposure to certain toxins and which is typically characterized early-on by increased membrane permeability and cell rupture.

Epidermal Growth Factor (EGF) and Its Receptor (EGF-Rc)

Human Epidermal Growth Factor is commercially available in a highly purified form, for example, from Upstate Biotechnology, Inc. (Lake Placid, N.Y.)(Lot No. #01-107C). This protein ligand is known to bind specifically and with high affinity to receptors located on the surface of EGF-responsive cells. Expression of the EGF-Rc is increased in EGF-responsive cancer cells, including breast cancer and prostate cancer cells.

Recent studies have demonstrated that the EGF-Rc is physically and functionally associated with Src protooncogene family protein tyrosine kinases (PTK) to form transmembrane receptor tyrosine kinases with ancillary signal transducing functions. This association is believed to be an integral part of the signalling event mediated by the EGF-Rc and may contribute to malignant transformation. SRC family PTK in the EGF-Rc-PTK complexes act as signal transducers and couple EGF-Rc to downstream cytoplasmic signalling pathways.

For use in the conjugates of the present invention, recombinant human EGF (hrEGF) is preferred, although it is anticipated that hEGF and hEGF analogs that specifically bind hEGF-Rc on cancer cells and induce EGF-associated tyrosine kinase activity will similarly inhibit cancer cell growth when conjugated to genistein or similar isoflavone tyrosine kinase inhibitors.

Production and Purification of EGF-Genistein Conjugates

Preferred conjugates of the invention are formed by linking an effective cytotoxic amount of isoflavone tyrosine kinase inhibitor, e.g., genistein molecules, to each molecule of EGF. For example, a reagent useful in the practice of the invention is a composition containing at least a 1:1 molar ratio of EGF:genistein, e.g. having at least one genistein molecule per EGF molecule. Preferably, the inventive composition contains at least a 1:3 molar ratio of EGF:genistein, e.g., having at least three genistein molecules per EGF molecule. The published photochemical conjugation method used for preparation of a B43-genistein immunoconjugate reported in Uckun et al., *Science*, 267:886, 1995 can be employed to generate an EGF-genistein conjugate. A cartoon depicting the primary structure of rhEGF conjugated with genistein is shown in FIG. 1.

One method for preparing the EGF-Genistein conjugate of the invention involves a two-step procedure, using the hetero-bifunctional photoreactive linking agent Sulfo-SANPAH (Pierce Chemical Co., Rockford, Ill.) which contains an N-hydroxysuccinimidyl ester and a m-nitro aryl azide on either terminus, as shown in FIG. 2. In the first step, incubation of the purified rhEGF with Sulfo-SANPAH at a 10:1 molar ratio of Sulfo-SANPAH:rhEGF forms amide linkages between free amino groups and the activated succinimidyl ester of Sulfo-SANPAH. Excess bifunctional linker is removed, e.g., by size-exclusion chromatography. Photolytic generation of a reactive singlet nitrene on the other terminus of the bifunctional linker in the presence of a 10-fold molar excess of genistein in DMSO then covalently incorporates the genistein into the conjugate at each of the three lysine residues. The singlet nitrene intermediate that was generated upon exposure to longwave UV light is preferentially inserted into the oxygen-hydrogen bonds of the C7-hydroxyl group of genistein. Excess genistein is removed, e.g., by size-exclusion chromatography.

Other methods for preparing EGF-Genistein conjugates may similarly be utilized. These include, for example, those methods described below in Example 7.

It is commonly known to those skilled in the art that an isoflavone, such as genistein, can be modified to produce an amino-isoflavone which can be linked to proteins such as EGF using common bifunctional linking agents. Such common bifunctional linking agents would include, for example, M-succinimidyl 3-(2-pyridyldithio)propionate, 4-succinimidyloxycarbonyl-methol-(2-pyridyldithio)-toluene, and N-succimidyl 6-[3-(2-pyridyldithio)propionamido]hexanoate.

Therapeutic Use of the Conjugates

The EGF-isoflavone tyrosine kinase inhibitors of the present invention are useful to inhibit the proliferation of cancer cells expressing EGF-Rc. The EGF receptor is known to be over expressed in tumors of the brain, bladder, breast, stomach, cervix and ovary. In breast, lung and bladder tumors, over-expression of the EGF receptor is an indicator of poor prognosis.

Administration of the inventive EGF-genistein conjugates to metastatic cells expressing EGF-Rc effectively induces apoptosis. This induced cell killing effect of the EGFgenistein conjugate is demonstrated in the Examples below, in EGF-Rc expressing breast cancer and prostate cancer cell lines, as well as in SCID mice having human breast tumor xenografts. Mutant C.B.17 mice with severe combined immunodeficiency (SCID) xenografted with human cancer cells is a recognized model system for examining therapeutic treatment of cancer (Mosier et al, 1988, Nature, 335:256; Uckun et al., 1995, Blood, 85:873–878.

The conjugates of the present invention, when administered to a patient having cancer cells expressing EGF-Rc in a therapeutically effective amount and manner, bind to EGF-Rc present on the cancer cells. Binding of the conjugate to the receptor brings the isoflavone tyrosine kinase inhibitor in contact with the specific kinase it inhibits, and in a manner that accelerates the "on" time of the otherwise weak, reversible inhibitor. The inhibitor is held in close approximation to the EGF-Rc associated tyrosine kinase complex by the inhibitor's covalent attachment to the EGF.

Administration of the Conjugates

The conjugates of the present invention can be formulated as pharmaceutical compositions and administered to a mammalian host, including a human patient in a variety of forms adapted to the chosen route of administration and suitable for administration of the protein-conjugate. Preferred administration routes include orally, parenterally, as well as intravenous, intramuscular or subcutaneous routes.

It is preferred that the conjugate of the present invention be administered parenterally, i.e. intravenously or intraperitoneally, by infusion or injection. Solutions or suspensions of the conjugates can be prepared in water, isotonic saline (PBS) and optionally mixed with a non-toxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of non-toxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for examples, sugars, buffers, or sodium chloride. Prolonged absorption of the injectable compositions can be brought about by the inclusion in the composition of agents delaying absorption, for example, aluminum monosterate hydrogels and gelatin.

Sterile injectable solutions are prepared by incorporating the conjugates in the required amount in the appropriate solvent with various other ingredients as enumerated above, and as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

The doses of the conjugates to be administered can vary widely in accordance with the size, age and condition of the patient to be treated. Useful dosages of the conjugates are those which will yield systemic exposure levels (i.e., area under serum concentration×time curve) of 0.28 μg/Lxhr or greater. Systemic exposure levels can be optimize din an individual patient by simply adjusting the dose according to the measured conjugate concentrations in the serum. Based on the monkey pharmacology data contained in this application, effective exposure levels are expected to be achieved with doses as low as 25 μg/kg.

The invention will be further described by reference to the following detailed examples.

EXAMPLE 1

Preparation and Characterization of EGF-Genistein Conjugate

The published photochemical conjugation method for preparation of the B43-genistein conjugate as described in Uckun et al., Science, 267:886–891, 1995, was employed to generate an EGF-genistein conjugate. This method involved a two step procedure using the hetero-bifunctional photoreactive cross-linking agent Sulfo-SANPAH, which contains an N-hydroxysuccinimidyl ester and an m-nitro aryl azide on either terminus. The reaction procedure is shown in FIG. 2. In the first step, highly purified, endotoxin-free rhEGF (lot no. #01-107C, Upstate Biotechnology, Lake Placid, N.Y. was incubated with the succinimidyl-containing photoreactive (optimal photolysis at 265–400 nm) bifunctional linking agent, Sulfo-SANPAH (40 mM solution in DMSO) (Pierce Chemical Co., Rockford, Ill.) at 10:1 molar ratio of Sulfo-SANPAH:rhEGF to form amide linkages between free amino groups and the activated succinimidyl ester of Sulfo-SANPAH. Excess linking agent was removed by passing the reaction mixture through a PD-10 prepacked G25 column (Pharmacia LKB, Piscataway, N.J.). Photolytic generation of a reactive singlet nitrene on the other terminus of the EGF-linking agent in the presence of a 10-fold molar excess of genistein in DMSO (Gen; MW 270.2, Calbiochem, LaJolla, Calif.) (50 mM solution in DMSO) then covalently incorporated the genistein into the conjugate. The mixture was irradiated with gentle mixing for ten minutes, with UV light at wavelengths of 254–366 nm using a multiband UV light emitter (Model UVGL-15 Mineralight, UvP, San Gabriel, Calif.). The singlet nitrene intermediate was generated upon exposure to longwave ultraviolet (UV) light and was preferentially inserted into the oxygen-hydrogen bonds of the C7-hydroxyl group of genistein. Excess genistein was removed by passage through a PD-10 column.

EXAMPLE 2

Binding of EGF-$^{125}$I-Genistein to EGF-R Positive Breast Cancer Cells

As shown in Table 1, radioiodinated EGF-Genistein was able to specifically attach to EGF-Rc positive MDA-MD-231 and BT-20 breast cancer cells with 4.5–5.7 molecules specifically binding to each cell, but it did not bind at detectable levels to EGF-Rc negative HL60 or NALM-6 leukemia cells.

TABLE 1

Selective Binding of EGF-Genistein to Cancer Cells

| Cell Line | % Inhibitable Binding | Specific Binding cpm/$10^8$ Cells | Molecules/Cell |
|---|---|---|---|
| MDA-MB-231 | 56 | 2548 | $4.5 \times 10^6$ |
| BT-20 | 65 | 4848 | $5.7 \times 10^6$ |
| NALM-6 | <1 | <10 | Not Evaluable |
| HL60 | <1 | <10 | Not Evaluable |

The specific activity of radioiodinated EGF-Genistein was $1.7 \times 10^5$ cpm/nmol. Binding of EGF-$^{115}$I-Gen to cancer cells was determined in the presence and absence of 100-fold molar excess of non-radioactive EGF-Gen. Each determination was performed in duplicate. Binding data are expressed as percentage of inhibitable binding (100% binding was the value obtained in the absence of excess unlabeled EGF-Gen), cell associated specific cpm inhibitable by excess unlabeled EGF-Gen, and number of EGF-Gen molecules bond per cell.

EXAMPLE 3

EGF-Genistein Conjugate Inhibits EGF-Rc Associated Protein Tyrosine Kinase Activity The effect of the EGF-genistein conjugate on the autophosphorylation of the EGF-Rc and on protein tyrosine kinase activity of the Src kinase associated with the EGF-Rc was examined. The breast cancer cell lines MDA-MB-231 (ATCC HTB-26) and BT-20 (ATCC HTB-19) were utilized in this study.

MDA-MB-231 cells were treated overnight with EGF-genistein conjugate at doses of 0.1, 1.0 and 10.0 µg/ml or with a control conjugate which does not react with the EGF-Rc, at 10 µg/ml, granulocyte colony stimulating factor (G-CSF)-genistein. G-CSF-genistein was prepared in the same way EGF-Genistein was prepared. The cells were stimulated with EGF (20 ng/ml) for five minutes, lysed in 1% NP-40 buffer, and the cell lysates were immunoprecipitated with anti-EGF-Rc antibody which recognizes the sequence of Ala$^{351}$-Asp$^{364}$ of the human EGF-Rc (UBI Catalog #05-104). The EGF-Rc immune complexes were then subjected to anti-phosphotyrosine Western blot analysis, as described (Uckun et al., 1993, *J. Biol. Chem.*, 268:21172–21184).

Figure 4A:
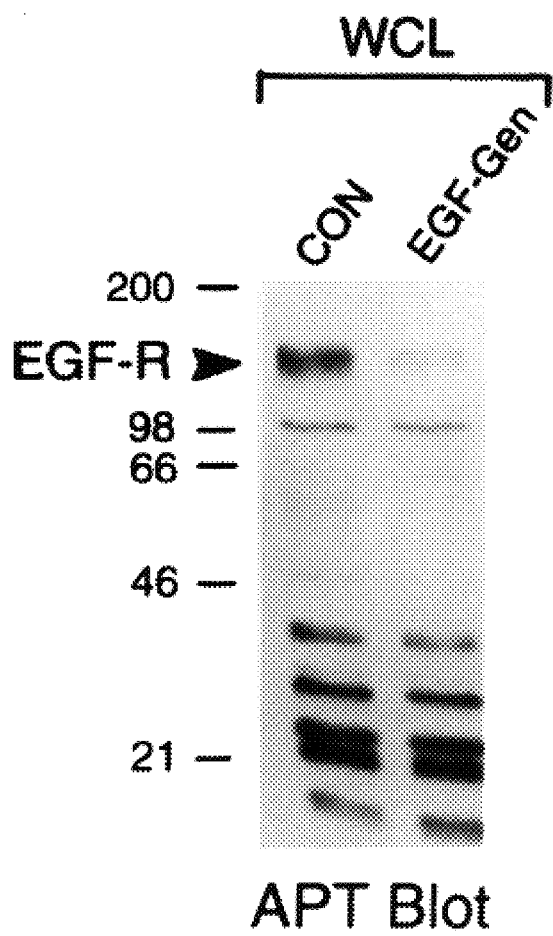
FIGS. 4A and 4B are autoradiograms of Western blots showing autophosphorylation of BT-20 cellular EGF-Rc in response to EGF stimulation and in the presence of EGF-genistein or control compounds.
Figure 4B:
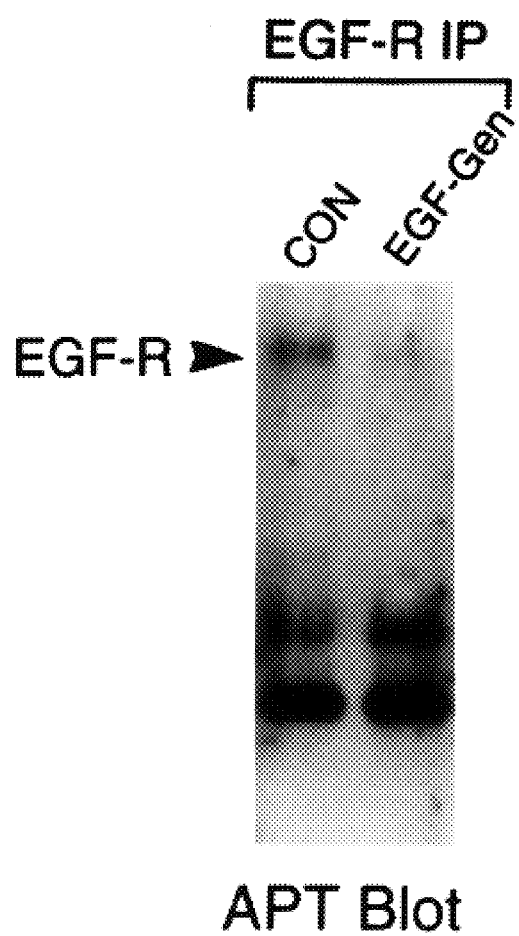

EGF-genistein treatment resulted in decreased autophosphorylation of the EGF-Rc in response to EGF in a dose-dependent fashion, whereas G-CSF-genistein had no effect. These results are shown in FIG. 3. Similar results were obtained after treatment of BT-20 cells with 10 µg/ml EGF-genistein, as shown in FIG. 4. Furthermore, assay of Src immune complex kinase activity, performed on the same BT-20 lysates, showed markedly reduced Src kinase activity as measured by autophosphorylation of the immunoprecipitated SRC kinase (see FIG. 5). In comparison, G-CSF-genistein at 10 µg/ml did not affect the autophosphorylation of the EGF-Rc or Src kinase. The data indicate that EGF-genistein is a potent and EGF-Rc specific protein tyrosine kinase inhibitor.

EXAMPLE 4

Selective Cytotoxicity of EGF-genistein, in vitro

The anti-cancer activity of EGF-genistein conjugate was established using EGF-Rc positive breast cancer and prostate cancer cell lines obtained from the ATCC and analyzed using in vitro clonogenic assays. The cells lines PC-3 (ATCC CRL-1435) and DU-145 (ATCC HTB-81) are androgen-insensitive prostate cancer cell lines. The cell lines MDA-MB231 (ATCC #TB-26) and BT-20 (ATCC HTB-19) are breast cancer cell lines. The EGF-Rc negative leukemia cell line NALM-6 was used as a control. As shown in Table 2, 24 hour treatment with 10 µg/ml EGF-genistein conjugate killed more than 99% of clonogenic MDA-MB-231, BT-20, PC3, and DU-145 cells under conditions which did not affect the clonogenic growth of EGF-Rc negative NALM-6 leukemia cells. Unlike the EGF-genistein conjugate, neither EGF (10 µg/ml, unmodified or Sulfo-SANPAH-modified) nor genistein (10 µg/ml), when used alone, were able to inhibit the clonogenic growth of the EGF-Rc-positive cancer cell lines. Similarly, G-CSF-genistein (10 µg/ml) did not affect the clonogenic growth of these breast and prostate cancer cell lines.

Figure 6:
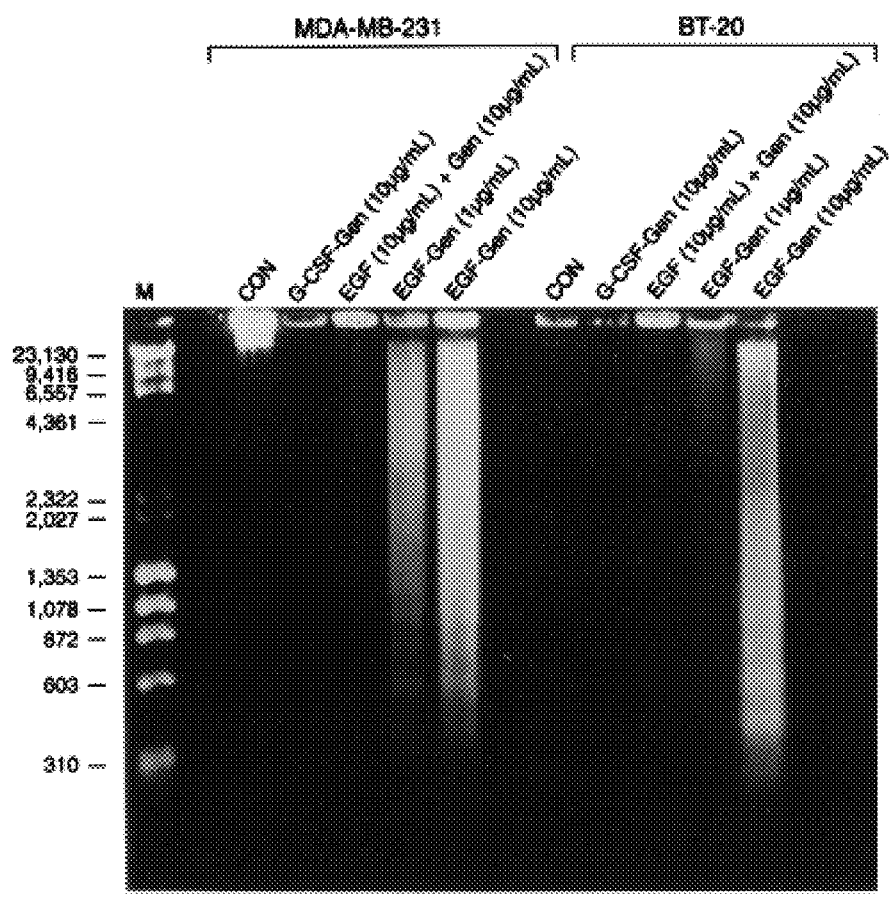
FIG. 6 is a photograph of an agarose gel showing results of a DNA fragmentation assay for apoptosis of human breast cancer cells treated with EGF-genistein and control compounds.

EGF-genistein conjugate was found to induce apoptotic cell death in EGF-Rc-positive breast cancer cell lines, as measured by DNA fragmentation assays. The DNA fragmentation assays were those as described by Waddick et al., 1995, *Blood*, 86:4228–4233. As shown in FIG. 6, DNA from Triton-X-100 lysates of EGF-genistein conjugate treated MDA-MB-231 or BT-20 breast cancer cells showed a ladder-like fragmentation pattern, consistent with apoptosis. No apoptosis was observed after treatment with unconjugated genistein or the control G-CSF-genistein conjugate.

TABLE 2

Cytotoxic Activity of EGF-Genistein Against Prostate Cancer and Breast Cancer Cell Lines

| Cell Line | Treatment | Mean No. Colonies Per $1 \times 10^5$ Cells | Percent Inhibition of Clonogenic Cells |
|---|---|---|---|
| MDA-MB-231 Breast Cancer | PBS | 395(368, 420) | — |
| | EGF, 10 µg/mL | 524(512, 536) | 0.0 |
| | Gen, 10 µg/mL | 275(268, 282) | 30.2 |
| | EGF-Gen, 1 µg/mL | 272(228, 315) | 31.0 |
| | EGF-Gen, 10 µg/mL | 0(0, 0) | >99.4 |
| | GCSF-Gen, 10 µg/mL | 395(390, 400) | 0.4 |
| BT-20 Breast Cancer | PBS | 155(143, 167) | — |
| | EGF, 10 µg/mL | 161(152, 170) | 0.0 |
| | Gen, 10 µg/mL | 117(113, 121) | 24.5 |
| | EGF-Gen, 1 µg/mL | 74(69, 79) | 52.3 |
| | EGF-Gen, 10 µg/mL | 0(0, 0) | >99.4 |
| | GCSF-Gen, 10 µg/mL | 154(150, 158) | 0.6 |
| PC-3 Prostate Cancer | PBS | 298(287, 309) | — |
| | EGF, 10 µg/mL | 355(307, 403) | 0.0 |
| | Gen, 10 µg/mL | 256(253, 259) | 14.1 |
| | EGF-Gen, 1 µg/mL | 5(3, 7) | 98.3 |
| | EGF-Gen, 10 µg/mL | 0(0, 0) | >99.7 |
| | GCSF-Gen, 10 µg/mL | 309,(298, 320) | 0.0 |
| DU-145 Prostate Cancer | PBS | 545(512, 578) | — |
| | EGF, 10 µg/mL | 744(724, 764) | 0.0 |
| | Gen, 10 µg/mL | 331(319, 343) | 39.3 |
| | EGF-Gen, 1 µg/mL | 0(0, 0) | >99.8 |
| | EGF-Gen, 10 µg/mL | 0(0, 0) | >99.8 |
| | GCSF-Gen, 10 µg/mL | 560(544, 576) | 0.0 |

TABLE 2-continued

Cytotoxic Activity of EGF-Genistein Against
Prostate Cancer and Breast Cancer Cell Lines

| Cell Line | Treatment | Mean No. Colonies Per 1 x 10⁵ Cells | Percent Inhibition of Clonogenic Cells |
|---|---|---|---|
| NALM-6 Pre-B All EGFR$_c$(-) | PBS | 214(209, 219) | — |
| | Gen, 10 µg/mL | 175(162, 188) | 18.2 |
| | EGF-Gen, 1 µg/mL | 223(195, 251) | 0.0 |
| | EGF-Gen, 10 µg/mL | 210(187, 233) | 0.0 |
| | B43-Gen, 10 µg/mL | 0(0, 0) | >99.5 |

Tumor cells were treated with the indicated agents for 24 hours at 37° C., washed twice, and then plated in duplicate Petri dishes at $10^5$ cells/mL. The clonogenic medium was alpha-MEM supplemented with 0.9% methylcellulose, 30% fetal bovine serum, and 50 µM 2-mercaptoethanol. Colonies were enumerated on day 7 using an inverted phase microscope of high optical resolution.

EXAMPLE 5

Toxicity Anti-tumor Activity of the Conjugate EGF-genistein, in vivo

Maintenance of SCID Mouse Colony

The SCID mice were housed in an American Association for Accreditation of Laboratory Animal Care (AAALAC)-approved specific pathogen-free facility assigned to the Biotherapy Program; animal care and veterinary oversight provided by the Department of Research Animal Resources according to the Guide for the Care and Use of Laboratory Animals (NIH, 1985). Animal housing was in a secure indoor facility with controlled temperature, humidity and noise levels. Ventilation consists of 12–20 air-changes per hours of unrecirculated air. Lighting is provided by fluorescent lights. A light/dark cycle of 12 hours each is strictly adhered to as is a room temperature of 70–75° C. The SCID mice were housed in microisolater cages which are autoclaved with rodent chow. The specific pathogen-free (SPF) environment is ensured by use of MICRO-ISOLATOR cages (Lab Products, Inc.) which are autoclaved complete with rodent chow (Purina Mills, Inc.) and hardwood Sani-Chips (P.J. Murphy Forest Products Corp.) for bedding. Water is provided ad libitum and is also autoclaved and acidified using 0.1% HCl. 22.75 mL of Bactrim (0.89 mg/mL sulfamethoxazole, 0.18 mg/mL trimethoprime) is added to each liter of water three days per week as a prophylaxis. Animals remain within the confines of the Micro-Isolators, except for scheduled cage changes and treatments, which are performed in a laminar flow hood. The CB.17 SCID mice (both males and females, 16–20 grams, 7–10 weeks) were produced by specific pathogen-free breeders in a SCID mouse breeding facility. The breeding colony was derived from CB17Icr SCID/+breeder pairs kindly supplied from McLaughlin Research Institute. The homozygosity and integrity of the strain of these inbred mice is maintained by allowing only brother/sister matings to occur. "Leaky" mice capable of substantial IgM production are not used in the experiments.

The primary tumor masses in the control mice were poorly circumscribed, fingering into the adjacent skeletal muscle and composed of sheets of closely packed cells interspersed with large areas of necrosis. In some areas, the sheets of cells were subdivided into complete nests and islands by short, thin fibrovascular septa. In other areas, the cells were found in solid sheets and short, indistinct streams. The morphologic features of the neoplastic cells were consistent with poorly differentiated adenocarcinoma. The nuclei were large, ovoid to irregularly spindle-shaped, and showed marked anisocytosis. The nuclei were vesicular or had finely reticular chromatin with multiple small condensations, and contained 1–2 large, eosinophilic nucleoli. Mitotic figures were numerous. Metastatic foci were present in the lungs and in the renal pelvis.

Mice were monitored daily for health status and were sacrificed when they became moribund, developed tumors which impeded their ability to attain food or water, or at the end of the 20 weeks experiment. Primary endpoints of interest were event-free survival and survival outcome. Life table statistical methodology were one of the primary approaches to analysis. Estimation of life table outcome used the Kaplan-Meier procedure. Comparison of outcome between groups was done with the log rank test.

RESULTS

The effect of the EGF-genistein conjugate on the growth of breast cancer cells in a SCID mouse xenograft model was examined. EGF-Genistein was not toxic to SCID mice. None of the 27 mice treated with intraperitoneal injections ranging from 2 µg to 800 µg showed any signs of toxicity. These results were quite remarkable if one considers that a very significant portion of EGF-Genistein homes to liver and gut, as determined by biodistribution studies using radioiodinated EGF-Genistein. As shown in Table 3, which details the tissue-to-plasma equilibrium distribution ratio for linear binding (R) values, in healthy SCID mice as well as SCID mice xenografted with human MDA-MB-231 breast cancer cells, most of the injected EGF-Genistein was retained in the liver and spleen, as reflected by the high R-values for these organs. These combined tissue binding and toxicity results demonstrate that the EGF-Rc tyrosine kinase complexes are not critical to the survival of normal tissues expressing EGF-Rc, such as the liver.

TABLE 3

Tissue Distribution Parameters
for EGF-Genetics in SCID Mice

| Parameter | Healthy Mice | MDA Mice |
|---|---|---|
| R brain, ml/g | 0.048 | 0.051 |
| R heart, ml/g | 0.38 | 0.35 |
| R skin, ml/g | 0.20 | 0.15 |
| R bladder, ml/g | 0.80 | 2.23 |
| R muscle, ml/g | 0.11 | 0.09 |
| R bone marrow, ml/g | 0.53 | 0.42 |
| R stomach, ml/g | 1.00 | 1.13 |
| R spleen, ml/g | 5.28 | 3.87 |
| R lungs, ml/g | 1.44 | 0.84 |
| R kidney, ml/g | 0.93 | 0.86 |
| R liver, ml/g | 7.40 | 8.15 |
| R intestine, ml/g | 0.86 | 1.08 |
| R rest of body, ml/g | 0.0001 | 0.09 |
| R tumor, ml/g | N/A | 0.16 |

A flow-limited physiological pharmacokinetic model was used to characterize the tissue disposition of EGF-Genistein in mice. A set of differential equations describing the mass balances of each model compartment was used to estimate linear binding constants for each organ. These differential equations were simultaneously solved with the use of ADAPT II software. R, tissue-to-plasma equilibrium distribution ratio for linear binding.

Since EGF-genistein was very potent against cancer cells in vitro, we decided to use 0.2 μg (4,000-fold less than the highest non-toxic dose tested) and 2 μg (400-fold lower than the highest non-toxic dose tested) doses in efficacy studies.

Figure 7:
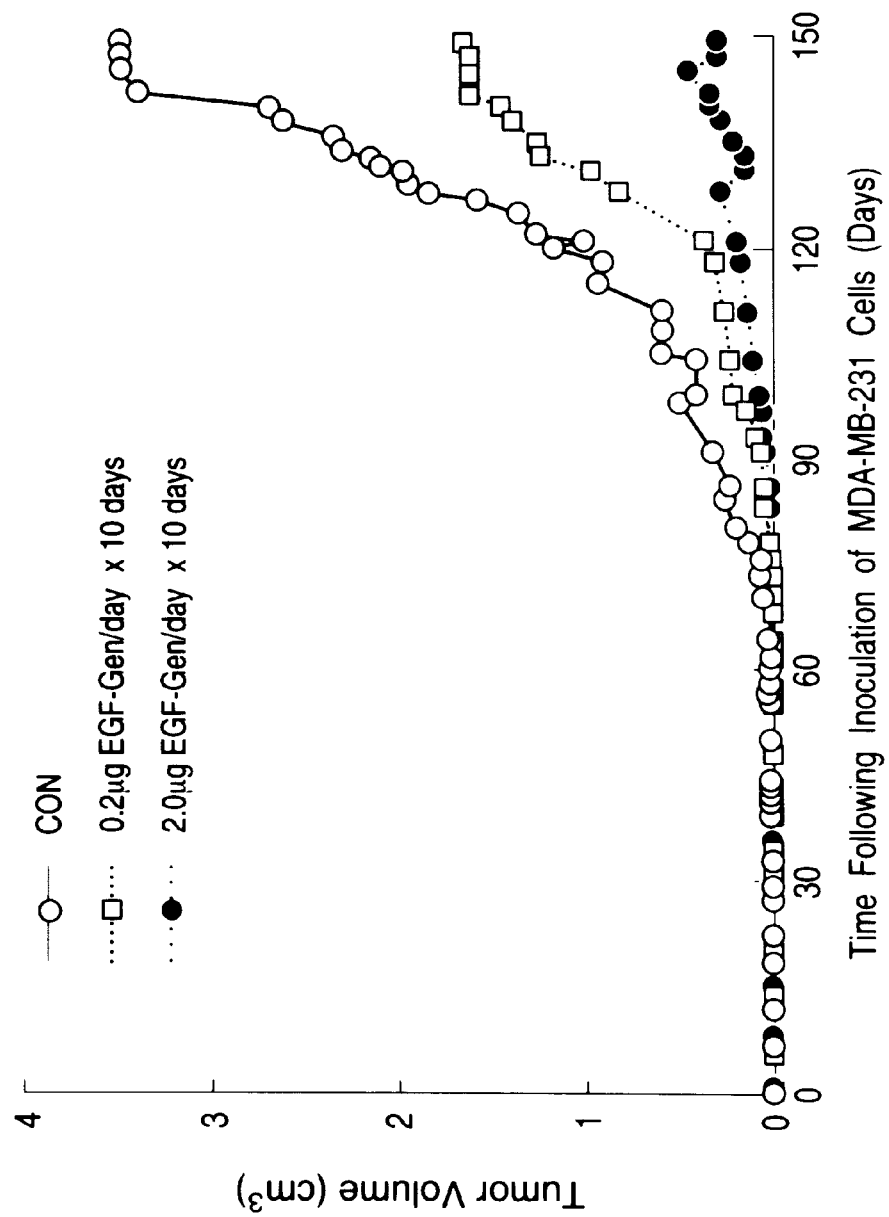
FIG. 7 is a graph showing the effects of EGF-genistein and control compounds on the progression of tumors in SCID Mice xenografted with human breast cancer cells.
Figures 8A, 8B:
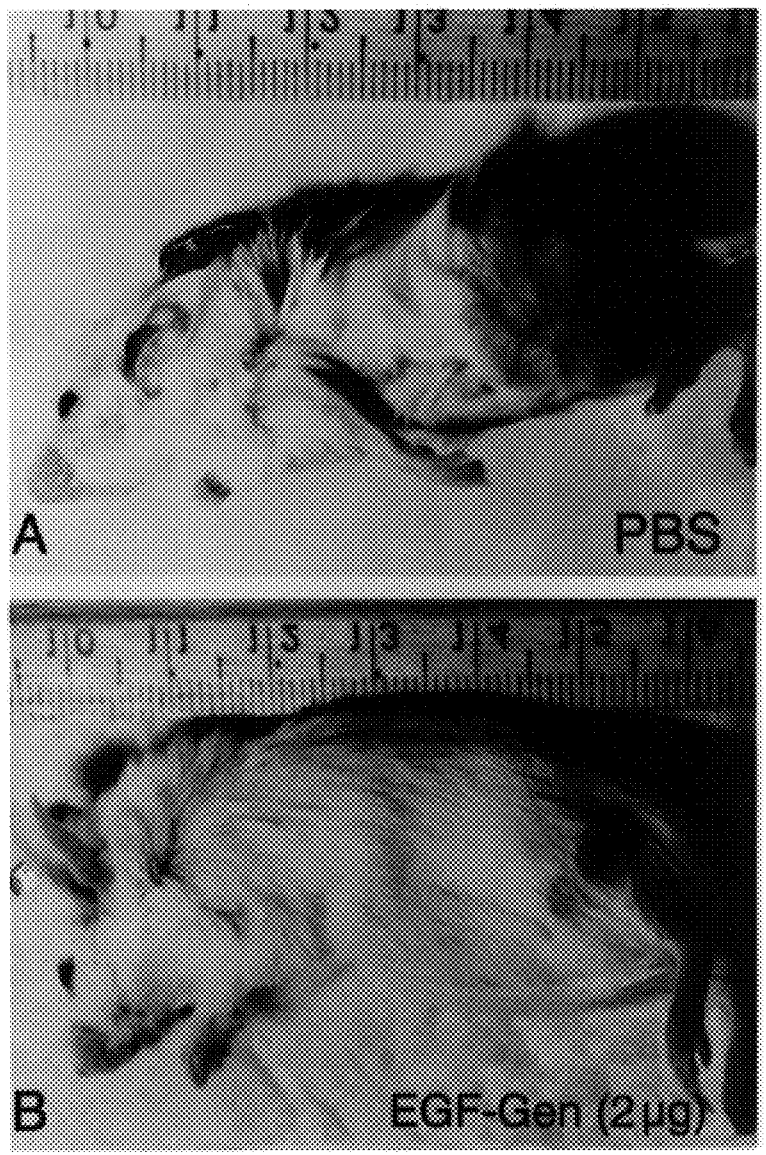
FIG. 8A is a photograph of a control, PBS-treated SCID mouse having a human breast cancer cell xenograft.
FIG. 8B is a photograph of an EGF-genistein-treated SCID mouse having a human breast cancer cell xenograft.

Thirty-nine control mice were treated for ten days with intraperitoneal injections of phosphate buffered saline (PBS), genistein and EGF (2 μg of each per day) or a G-CSF-genistein conjugate (2 μg/day). G-CSF-genistein conjugate was prepared as described for Example 3. Each of these 39 control mice developed rapidly growing tumors after subcutaneous innoculation of $5 \times 10^6$ MDA-MB-231 cells, as shown in FIGS. 7 and 8.

FIG. 9 shows the collective data on the survival advantage of SCID mice treated with EGF-Genistein (0.2 or 2 μg/mouse/day×10 days) as compared to (1) control mice (N=60) treated with PBS, G-CSF-Genistein (10 μg/mouse/day×10 days), or unconjugated Genistein (10 μg/mouse/day×10 days), (2) mice treated each day with 10 μg unconjugated Genistein (i.e., more than 1,000 fold higher dose of genistein than what is contained in 2 μg EGF-Genistein; 16.4 nmols vs 12.2 pmols) plus 10 μg unconjugated EGF (i.e., 5-fold higher dose of EGF than in 2 μg EGF-Genistein) for a total of 10 days, (3) mice treated with a single dose of 9.3 μg methotrexate, (4) mice treated with a single dose of 50 μg adriamycin, and (5) mice treated with a single dose of 1 mg cyclophosphamide. All drugs were administered as intraperitoneal injections in a 0.2 mL volume.

All of the 60 control mice died within 108 days with a median survival of 52 days (i.e., half of the mice were dead by 52 days and all of them were dead by 108 days), whereas 60±15% of EGF-Genistein treated mice survived beyond 210 days. The effects of EGF-Genistein were dose-dependent since a ten-fold lower dose was substantially less effective (FIG. 9). By comparison, the median survival times were 66.6 days for methotrexate-treated mice, 41.7 days for adriamycin-treated mice, and 79.7 days for cyclophosphamide-treated mice.

The inability of 10 μg EGF plus 10 μg Genistein to confer long-term survival in this SCID mouse model of metastatic human breast cancer demonstrates that (1) the anti-cancer activity of EGF-Genistein cannot be attributed to the EGF moiety alone and conjugation to EGF enhanced the potency of Genistein against breast cancer cells more than 1,000 fold; that is, 12 pmols of genistein, which is contained in conjugated form in the 2 μg of EGF-Genistein, was highly effective in the SCID mouse xenograft model of human metastatic breast cancer whereas 37,000 pmols of Genistein which is contained in 10 μg of unconjugated Genistein was not effective at all (see FIG. 9 and above discussion of survival outcome).

EXAMPLE 6

Pharmacodynamic Features of EGF-Genistein in SCID Mice and Monkeys

We examined the pharmacodynamic features of EGF-Genistein first in SCID mice with and without human breast cancer xenografts. Mice were injected either intravenously or intraperitoneally with 2 μg bolus dose of EGF-Genistein. At multiple time points after the injection, blood samples were collected and serum EGF-Genistein concentrations were determined using the Quantikine ELISA kit from R&D Systems. The systemic exposure level, as measured by the area under the concentration-time curve (AUC), achieved with 2 μg EGF-Genistein was 2.8 μg/L×hr. Thus, if one wants to achieve the therapeutic effect against human breast cancer elicited by 2 μg EGF-Genistein in clinical settings, then one would need to achieve an AUC of 2.8 μg/L×hr or greater. Because EGFGenistein was not toxic to mice even at doses as high as 800 μg/mouse, we postulated that such exposure levels could be achieved in monkeys. To test this hypothesis, we used three female cynomologous monkeys and gave them intravenous one hour infusions of EGF-Genistein, each receiving the drug at a specific dose level, namely, 25 μg/kg/day×10 days, 50 μg/kg/day×10 days, or 100 μg/kg/day×10 days. At multiple time points after the injection, blood samples were collected and serum EGF-Genistein concentrations were determined using the Quantikine ELISA kit from R&D Systems. Table 4 shows the pharmacokinetic parameters for the first and/or tenth doses at each dose level. The results were fitted to a one-compartment model. Notably, treatment with 100 μg/kg/day EGF-Genistein yielded an AUC of 13–16.9 μg/L×hr, which is much higher than the target AUC of 2.8 μg/L×hr which was found to be effective in the SCID mouse model of human breast cancer.

Throughout the monkey study, monkeys were monitored for signs of toxicity and their vital signs were determined daily on days 1–10 and twice weekly afterwards. Complete blood counts, serum chemistry profile, laboratory assays for kidney and liver function were obtained daily on days 1–10, 3×/week in the following week, and once weekly thereafter. No clinical or laboratory evidence of significant toxicity was observed in this study. Thus, EGF-Genistein concentrations higher than those which are required to elicit therapeutic efficacy against human breast cancer cells in vivo can be achieved in monkeys without toxicity. These results further confirmed that the EGF-Rc tyrosine kinase complexes are not critical to the survival of normal tissues expressing EGF-Rc, such as the liver.

TABLE 4

Pharmacokinetic Parameters of EGF-GEN in Monkeys

| Parameters | Monkey 52A | | Monkey 52B | Monkey 521 | |
| --- | --- | --- | --- | --- | --- |
| | Dose #1 | Dose #10 | Dose #10 | Dose #1 | Dose #10 |
| Dose (mg/kg/day) | 0.05 | 0.05 | 0.025 | 0.1 | 0.1 |
| Vc (L/kg) | 17.5 | 30.9 | 8.1 | 8.3 | 11.3 |
| Ke (1/hr) | 0.62 | 0.68 | 2.2 | 0.71 | 0.68 |
| T½β (hr) | 1.1 | 1.0 | 0.3 | 1.0 | 1.0 |
| Cl (L/hr/kg) | 10.8 | 21.0 | 18.1 | 5.9 | 7.7 |
| Cmax (ng/ml) | 2.9 | 1.2 | 0.9 | 12.0 | 6.1 |
| AUC (μg/L/day*hr) | 4.6 | 2.4 | 1.38 | 16.9 | 13.0 |

EXAMPLE 7

Regioselective Construction of EGF-Genistein Conjugate

Reagents containing genistein pre-linked through the C7-hydroxyl to a carbon chain that terminates in N-hydroxysuccinimide ester have been prepared. These compounds need only be incubated with the carrier proteins to affect amide bond formation between the protein's free amino side chains and the reagent's activated ester. This approach to the preparation of an EGF-genistein conjugate offers the advantage of a mild, one-step protein coupling procedure, regio-defined attachment of the genistein molecule to the EGF, ease of purification, and functional group versatility. The preparation of these new reagents relies on the synthesis of differentially hydroxyl-protected genistein.

Figure 10:
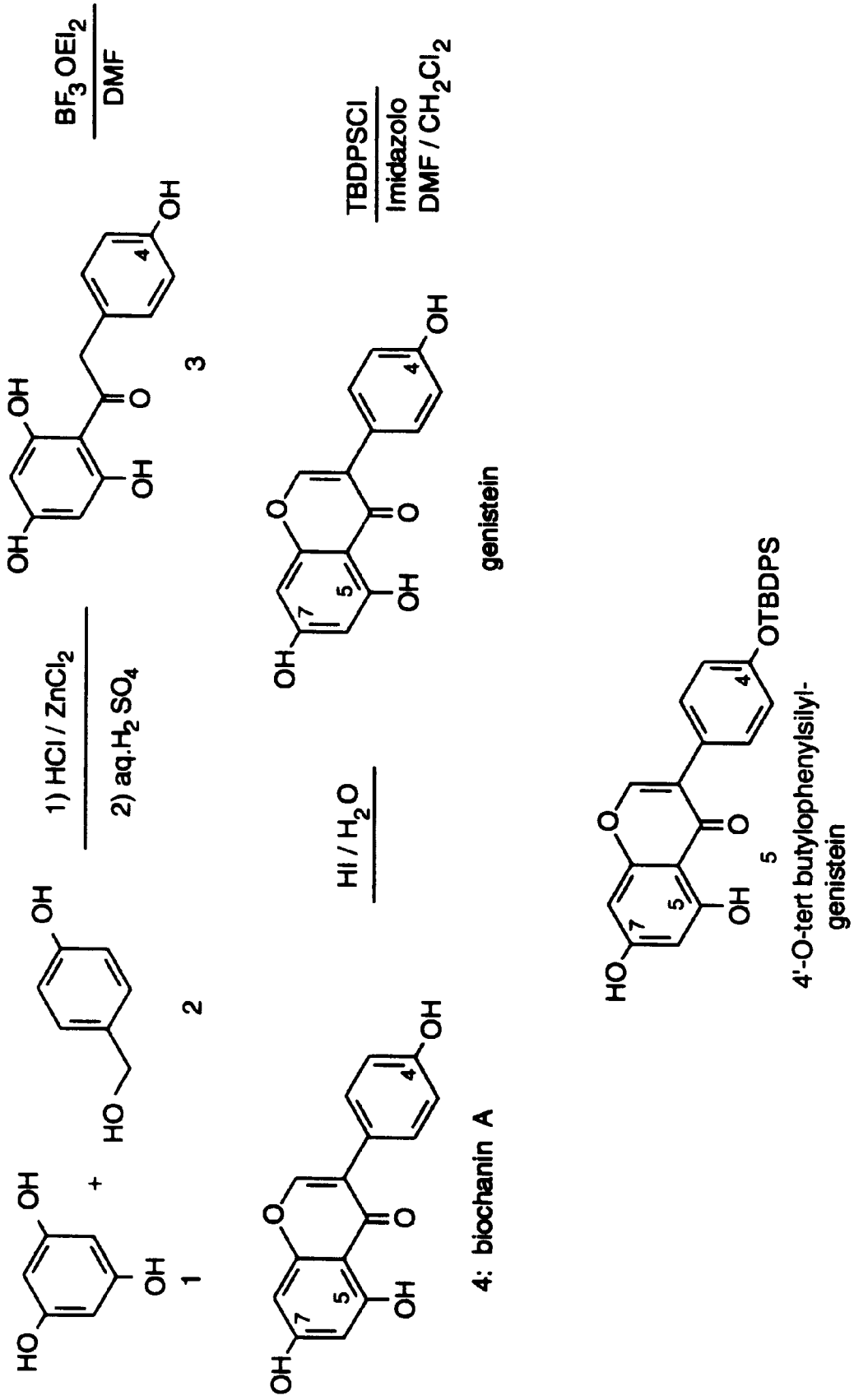
FIG. 10 is a schematic representation of a method for the synthesis of 7-O-tert-butyldiphenylsilyl-genistein.

The method described in Pelter et al., 1978, *Journal Chem.Soc*, Perkin Trans. I, 843, for the total synthesis via biochanin A (4'-O-methylgenistein), followed for demethylation provides a facile route to multi-gram quantities of genistein. Anhydrous phloroglucinol was condensed with p-methoxypheylacetonitrile under acidic conditions to give the acylated phloroglucinol product in high yield after hydrolysis of the ketimine hydrochloride. Formulation using DMF and $BF_3.OEt_2$ then gave biochanin A in about 40% overall yield after recrystalization. Demethylation in refluxing aqueous hydroiodic acid, followed by chromatography and crystallization from water provided synthetic genistein in 60–75% yield. The reaction scheme is shown in FIG. 10.

Figure 11:
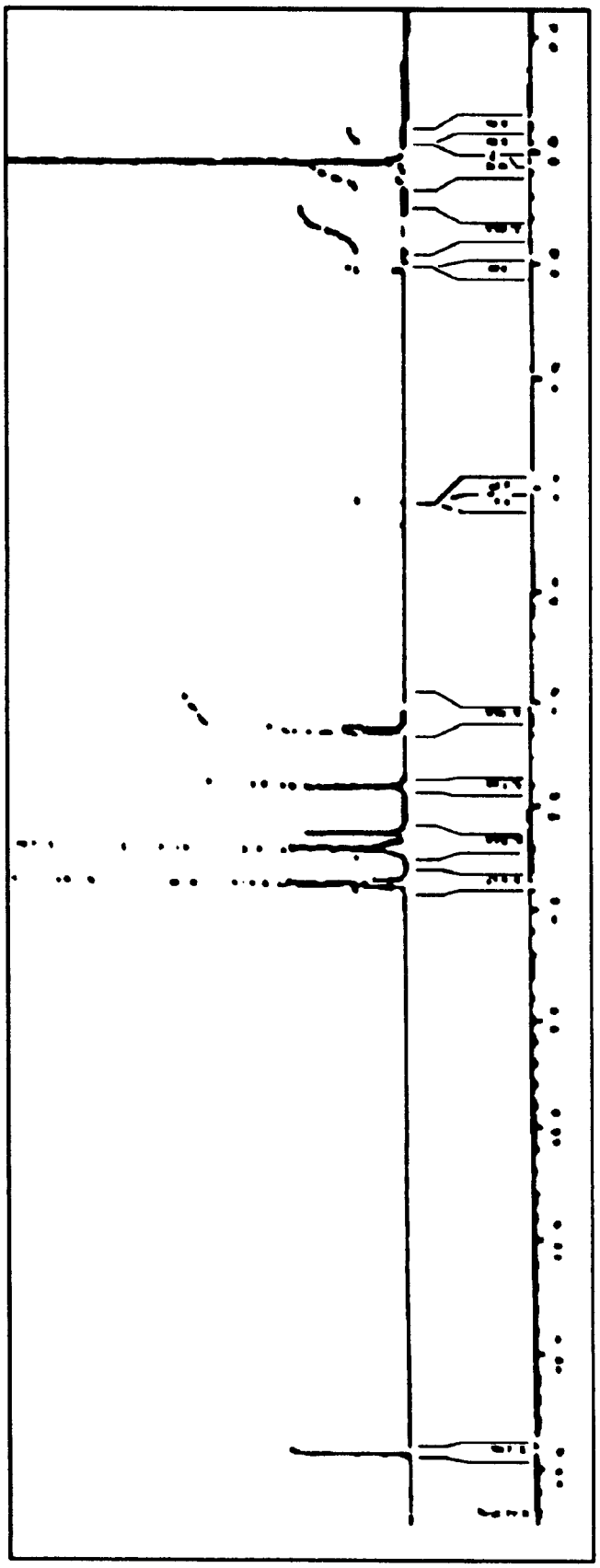
FIG. 11 is a $^1$HNMR spectrum of 7-O-tert-butyldiphenylsilyl-genistein.

It was anticipated that intramolecular hydrogen bonding of the C5 hydroxyl with the adjacent carbonyl would deactivate the C5 alcohol towards functionalization, but highly selective silylation of genistein with either tertbutyldimethylsilyl chloride (1.2 equivalence), or tertbutyldiphenylsilyl chloride in the presence of imidazole and in either $CH_2Cl_2$, dimethylformamide, or a combination of these solvents provides good yields (about 70–80%) of the chromatographically separable C4' silyl ether (using TEDPSCl), with little C4', C7 disilyl ether formed. The C4', C7 disilyl ether by-product that is generated is then regioselectively monodesilylated by treatment with p-toluenesulfonic acid in $CH_2Cl_2$—$CH_3OH$ to give back the C4' silyl ether. The structure of this compound was rigorously established by the observation of a unique nuclear Overhauser effect between the protons of the silicon methyl groups and the C3' protons in the $^1HNMR$ spectra, as shown in FIG. 11.

The ability to regioselectively and efficiently silylate only the C4' hydroxyl of genistein, and the inherent unreactivity of the C5 hydroxyl allows for specific functionalization of the C7 hydroxyl group. The silyl group is removed under mild and neutral conditions at the end of the synthesis by simple treatment with fluoride.

Figure 12:
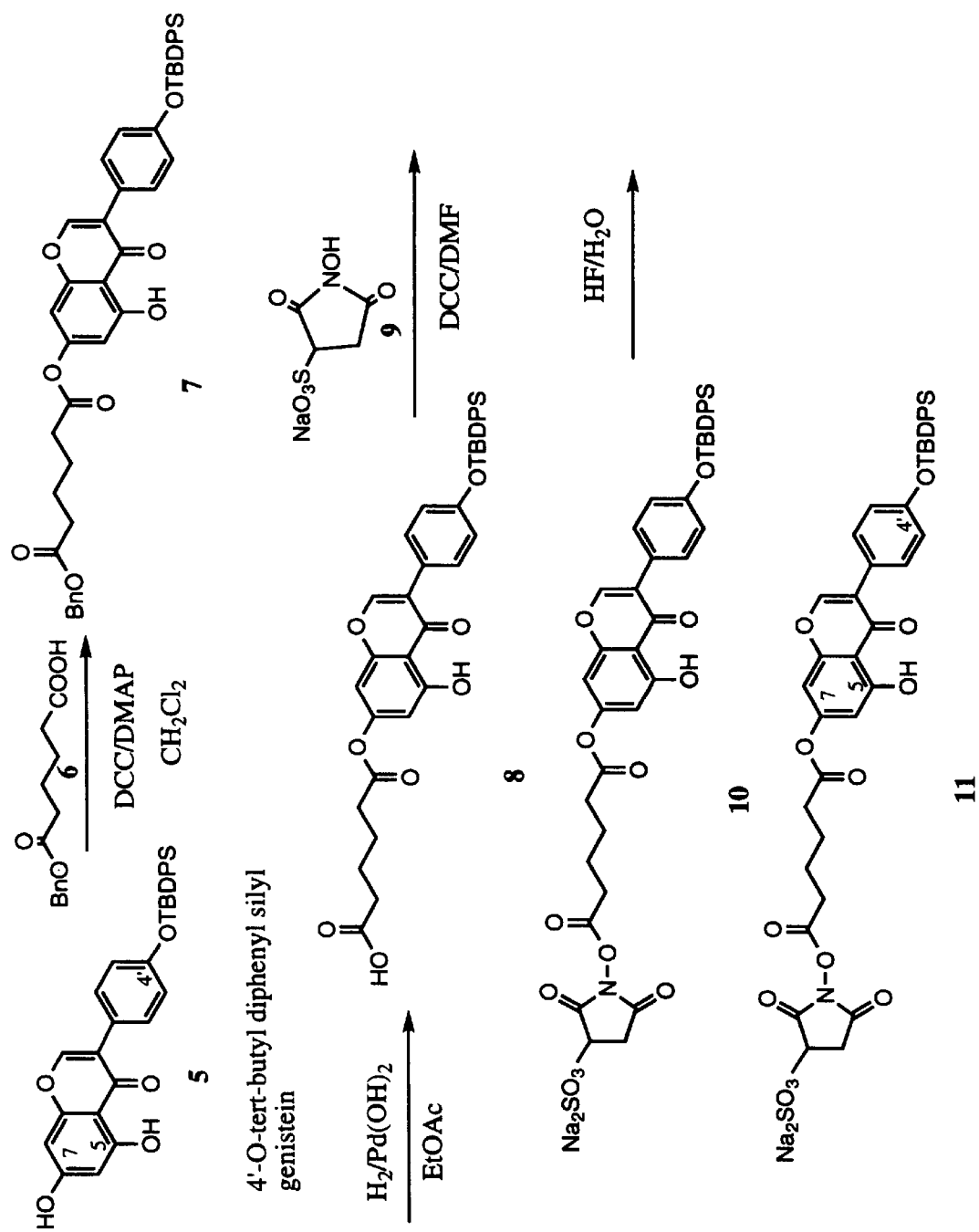
FIG. 12 is a schematic representation of a method for the synthesis of 7-O-genistein,N-O-sulfosuccinimidyladipate.

Four types of functional groups for the regiospecific linkage of 4'-O-tertbutyldiphenylsilylgenistein to EGF have been used. These include ester, carbonate, carbamate, ether and N-O ether. The C7 hydroxyl 4-O-tertbutyldiphenylsilylgenistein is efficiently and selectively functionalized in the presence of the free C5 hydroxyl. Esterification of 4-O-tertbutyldiphenylsilylgenistein by DCC coupling with mono-benzyladipate cleanly produced genistein ester, as shown in FIG. 12. Paladium-catalyzed hydrogenolysis of the benzyl ester then liberated the carboxylic acids. Carbodiimide-mediated esterification with the water soluble N-hydroxysuccinimide derivative gave activated ester. Removal of the Silyl ether by fluoride treatment then provided 7-O-genistein N-O-sulfosuccinimidyladipate.

Figure 13:
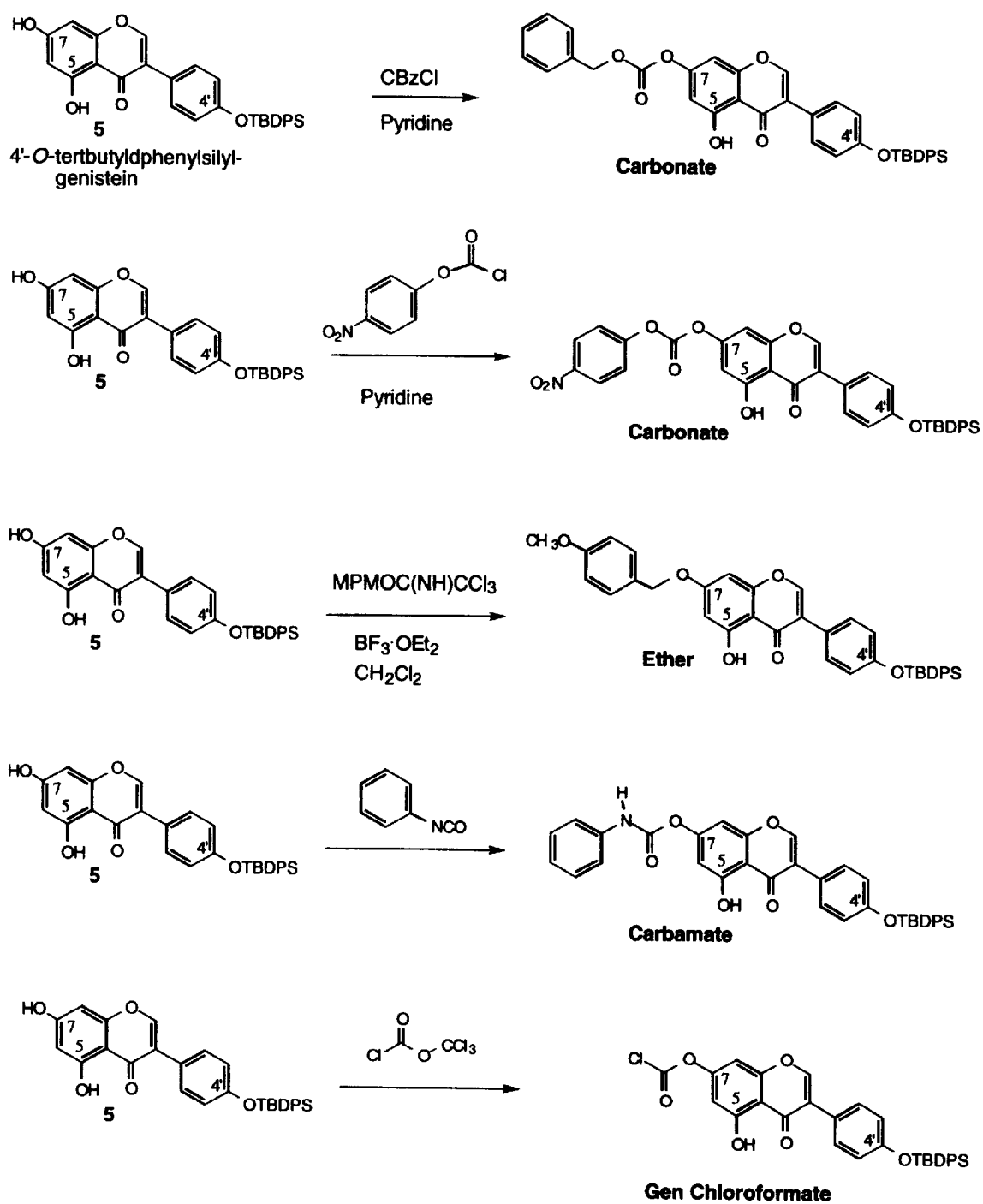
FIG. 13 is a schematic representation of methods for the regiospecific functionalization of 4'-O-tert-butyldiphenylsilylgenistein.

Because the ester linkage between the cross-linker and genistein may be susceptible to premature cleavage under physiological conditions in vivo, more stable connections at the C7 position, involving carbonates, ethers and carbamates were analyzed. As shown in FIG. 13, treatment of 4-O-tertbutyldiphenylsilylgenistein with carbobenzyloxychloride (CBzCl) or p-nitrophenylcholorformate yields the corresponding carbonates. Similarly, treatment of 4-O-tert-butyldiphenylsilylgenistein with methoxyphenylmethyl trichloroacetimidate and $BF_3.OEt_2$ gives the C7 p-methoxybenzyl ether, whereas treatment with phenylisocyanate yielded the C7 carbonate. Attempted carbamate formation by treating the p-nitrophenylgenistein carbamate with simple amines or amino acids gave 4-O-tertbuatyldiphenylsilylgenistein by elimination of the genistein moiety, rather than of p-nitrophenyl. Thus, genistein derived carbamates can best be derived from isocyanates and genistein, or from a genistein chloroformate and amine. The 7-O-chloroformate was prepared by treating genistein with diphosgene.

Figure 14:
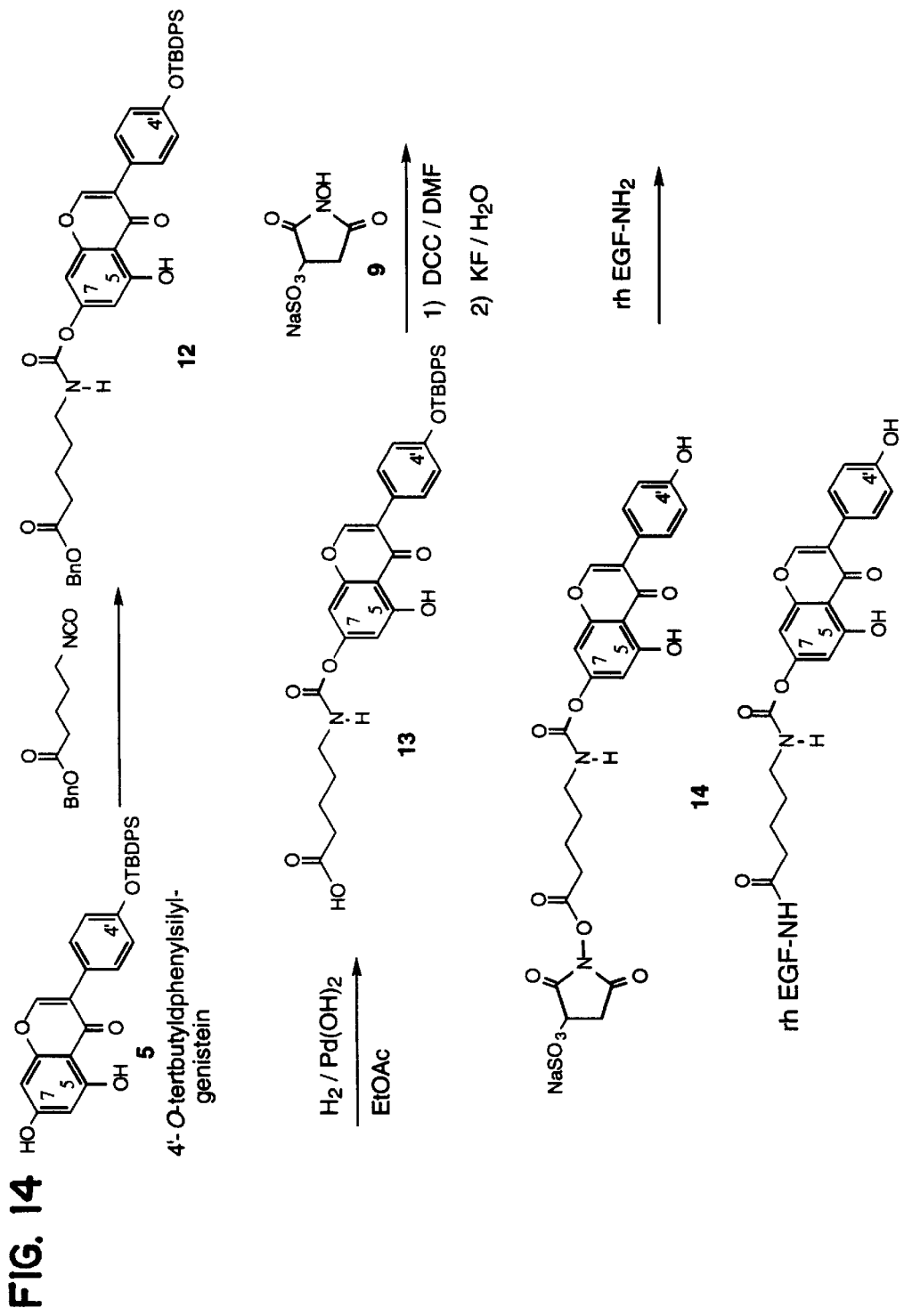
FIG. 14 is a schematic representation of a method for the synthesis of carbamate-linked EGF-genistein.

The synthetic design of carbamate-linked EGF-genistein is illustrated in FIG. 14. The compound 4-O-tertbutyldiphenylsilylgenistein was reacted with an isocyanate-benzyl ester, and the resulting compound was then converted into the succinimidyl ester. Incubation of the succinimidyl ester with EGF allowed amide formation to occur between the N-hydroxysuccinimide activated carboxylic acid and the amino side chains of EGF to form EGF-N-(5-aminocapramidoyl)-7-O-genistein carbamate. Neutralization of the three amino groups of rhEGF(Asn-1, Lys-28 and Lys-48) via amide formation allowed the amide-modified protein to be readily separated from any unfunctionalized protein by simple ion exchange chromatography. The extent of amine modification was quantified by simple colometric analysis, by the method described in Snyder et al., 1975, Anal. Biochem., 64:284–288, as well as by electrospray mass spectrometry as described in Straub et al., 1994, Bioconjugate Chem., 5:194–198.

Figure 15:
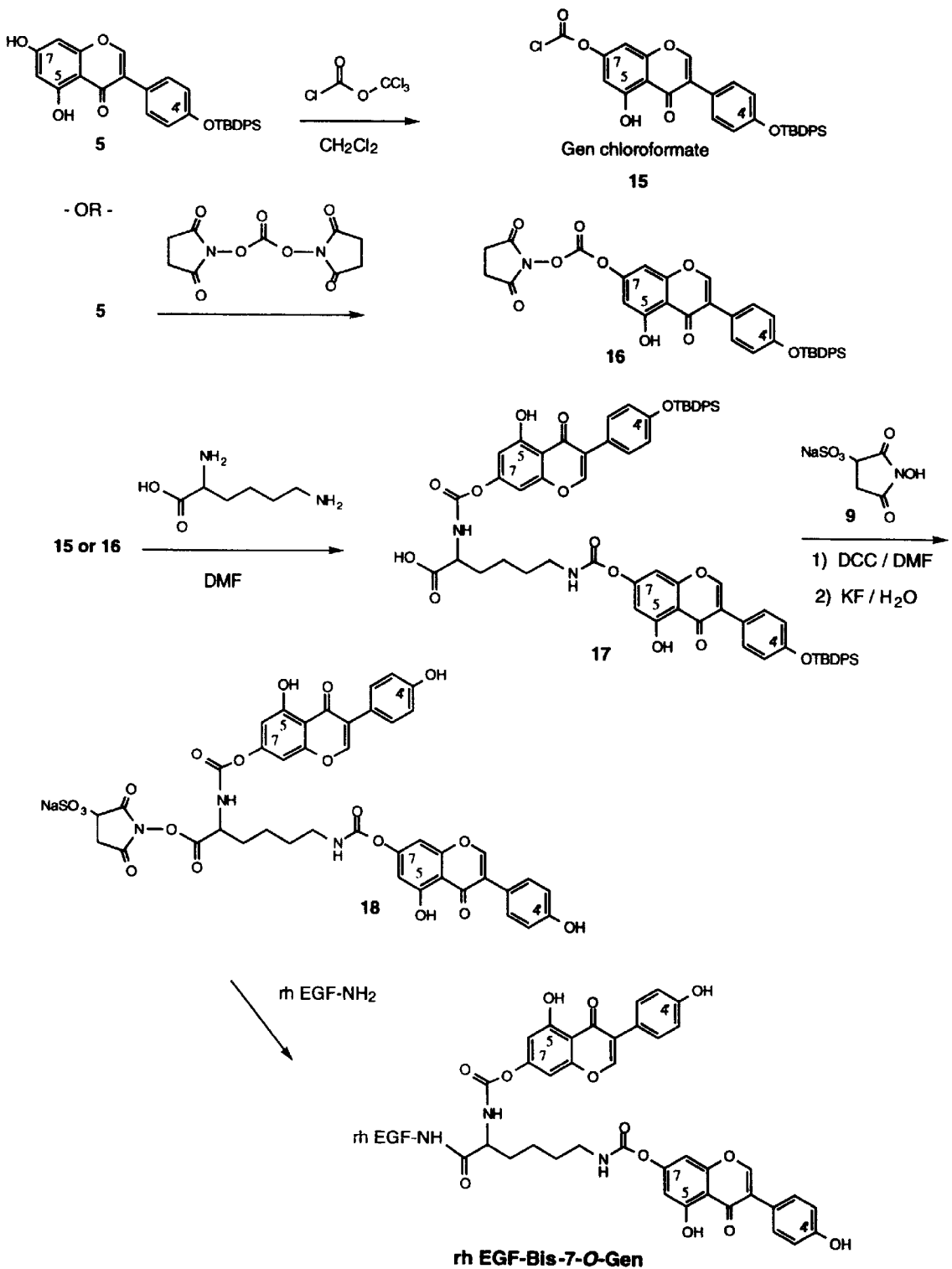
FIG. 15 is a schematic representation of a method for the synthesis of EGF-Bis-7-O-genistein.

Carbamate linkage may be used to prepare branched carrier molecules bearing two or more genistein molecules per point of EGF attachment. These compositions are prepared from a lysine cross-linker and 7-O-genistein chloroformate, or an activated carbonyl equivalent, according to the precedent of Monfardini et al., 1995, Bioconjugate Chem., 6:62–69, using a lysine linked polyethylene glycol. Amine addition to the p-nitrophenyl 7-O-genistein carbamate (FIG. 15) results in the competitive displacement of genistein rather than p-nitrophenyl. Thus, the more reactive 7-O-genistein chloroformate or N-hydroxysuccinimidyl carbonate of 7-O-genistein and lysine should be used to generate the lysine bis-7-O-genistein carbamate, as shown in FIG. 16. Activation of the lysine carboxylic acid via N-hydroxysuccinimide ester formation, followed by fluoride-induced desilyation yields an EGF modifying reagent carrying two genistein molecules. This method may be readily extended to incorporate higher degrees of branching to geometrically increase the carrying capacity of EGF for genistein. Practical considerations, such as solubility, will ultimately limit the extent of branching in PTK carrier molecules, but this approach will significantly enhance the carrying capacity of EGF for PTK inhibitors.

All publications, patents and patent documents are incorporated by reference herein, as though individually incorporated by reference. The invention has been described with reference to specific and preferred embodiments and techniques. However, it should be understood that many variations and modifications may be made while remaining within the spirit and scope of the invention.

I claim:

1. A composition comprising:
   tyrosine kinase inhibitor linked to epidermal growth factor (EGF), wherein the composition binds to EGF receptors present on the surface of a cell, and wherein the composition inhibits tyrosine kinases associated with the EGF receptor, thereby inducing apoptosis and clonogenic cell death.

2. The composition of claim 1 wherein the tyrosine kinase inhibitor is an isoflavone selected from the group genistein, daidzein, amino-genistein, and quercetin.

3. The composition of claim 1, wherein the tyrosine kinase inhibitor is genistein.

4. The composition of claim 1, wherein the tyrosine kinase inhibitor is 7-O-tert-butyldiphenylsilyl-genistein.

5. The composition of claim 3 wherein the tyrosine kinase inhibitor is covalently linked to the epidermal growth factor.

6. The composition of claim 1 wherein the tyrosine kinase inhibitor is linked to EGF by photoaffinity cross-linking.

7. The composition of claim 1 wherein the tyrosine kinase inhibitor is linked to EGF via an ester, carbonate, carbamate, or ether linkage.

8. The composition of claim 1 wherein the tyrosine kinase inhibitor is linked to the EGF via a carbamate linkage.

9. The composition of claim 1 comprising genistein covalently linked at its C7 position via a carbamate linkage to EGF.

10. The composition of claim 1 comprising two or more isoflavone tyrosine kinase molecules per EGF molecule.

11. A composition comprising genistein covalently linked to epidermal growth factor.

12. A composition comprising:

an isoflavone tyrosine kinase inhibitor linked to epidermal growth factor (EGF), wherein the composition binds to EGF receptors present on the surface of a cell, and said composition inhibiting EGF receptor tyrosine kinase and EGF receptor associated Src protooncogene family tyrosine kinases of the cell without directly effecting other cell tyrosine kinases and inducing cell apoptosis.

* * * * *